US012642969B2

(12) United States Patent
Dinsmoor

(10) Patent No.: US 12,642,969 B2
(45) Date of Patent: Jun. 2, 2026

(54) SPINAL CORD INJURY THERAPY BASED ON EVOKED COMPOUND ACTION POTENTIALS

(71) Applicant: Medtronic, Inc., Minneapolis, MN (US)

(72) Inventor: David A. Dinsmoor, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 482 days.

(21) Appl. No.: 17/810,459

(22) Filed: Jul. 1, 2022

(65) Prior Publication Data

US 2023/0047655 A1 Feb. 16, 2023

Related U.S. Application Data

(60) Provisional application No. 63/231,498, filed on Aug. 10, 2021.

(51) Int. Cl.
*A61N 1/36* (2006.01)

(52) U.S. Cl.
CPC ..... *A61N 1/36139* (2013.01); *A61N 1/36003* (2013.01); *A61N 1/36062* (2017.08)

(58) Field of Classification Search
CPC .............. A61N 1/0551; A61N 1/36139; A61N 1/36034; A61N 1/36135; A61N 1/36062; A61N 1/36031; A61N 1/36185; A61N 1/36003; A61N 1/36067; A61N 1/36125; A61N 1/05; A61N 1/3603; A61N 1/3606; A61N 1/36103; A61N 1/00; A61N 1/36535; A61N 1/04; A61N 1/02; A61N 1/18; A61N 1/3604; A61N 1/08; A61N 1/365;

(Continued)

(56) References Cited

U.S. PATENT DOCUMENTS

| 10,183,168 B2 | 1/2019 | Baru et al. |
| 10,568,559 B2 * | 2/2020 | Parker .................... A61B 18/14 |

(Continued)

FOREIGN PATENT DOCUMENTS

WO 2020124135 A1 6/2020

OTHER PUBLICATIONS

International Search Report and Written Opinion of International Application No. PCT/IB2022/057402 dated Nov. 18, 2022, 13 pp.

(Continued)

*Primary Examiner* — Deborah L Malamud

(74) *Attorney, Agent, or Firm* — Shumaker & Sieffert, P.A.

(57) ABSTRACT

Devices, systems, and techniques for controlling electrical stimulation therapy are described. In one example, a system is configured to deliver, via a first electrode combination, a first stimulation pulse to a portion of a spinal cord of a patient located caudally of a spinal cord injury location of the spinal cord of the patient; sense, via a second electrode combination, an evoked compound action potential (ECAP) signal elicited by the first stimulation pulse; identify, by processing circuitry, a characteristic of the ECAP signal; determine, by the processing circuitry and based on the characteristic of the ECAP signal, a therapy parameter value that at least partially defines a second stimulation pulse; and deliver the second stimulation pulse according to the determined therapy parameter value.

21 Claims, 8 Drawing Sheets

(58) Field of Classification Search

CPC ....... A61B 5/24; A61B 5/4836; A61B 5/4041; A61B 5/388; A61B 5/377; A61B 5/4848; A61B 5/7264; A61B 5/407; A61B 5/4082; A61B 5/05; A61B 5/112; A61B 5/4519; A61B 5/486; A61B 5/00

See application file for complete search history.

(56) References Cited

U.S. PATENT DOCUMENTS

| | | | |
|---|---|---|---|
| 10,926,092 B2 | 2/2021 | Esteller et al. | |
| 2014/0243926 A1 | 8/2014 | Carcieri et al. | |
| 2019/0099602 A1 | 4/2019 | Esteller et al. | |
| 2019/0168002 A1 | 6/2019 | Steinke et al. | |
| 2019/0209844 A1* | 7/2019 | Esteller ............. | A61N 1/36071 |
| 2019/0269919 A1 | 9/2019 | Brill et al. | |
| 2019/0269925 A1 | 9/2019 | Hershey et al. | |
| 2019/0388692 A1 | 12/2019 | Dinsmoor et al. | |
| 2020/0147397 A1 | 5/2020 | Huertas Fernandez et al. | |
| 2021/0187297 A1 | 6/2021 | Pulliam et al. | |

OTHER PUBLICATIONS

Chakravarthy et al., "Sensing Evoked Compound Action Potentials from the Spinal Cord: Novel Preclinical and Clinical Considerations for the Pain Management Researcher and Clinician," Journal of Pain Research, vol. 13, doi: 10.2147/JPR.S289098, Dec. 4, 2020, pp. 3269-3279.

Courtine et al., "Spinal cord repair: advances in biology and technology," Nature Medicine, vol. 25, doi.org/10.1038/s41591-019-0475-6, Jun. 2019, pp. 898-908.

Formento et al., "Electrical spinal cord stimulation must preserve proprioception to enable locomotion in humans with spinal cord injury," PMC, Nature Neuroscience, vol. 21, No. 12, doi:10.1038/s41593-018-0262-6, Dec. 2018, pp. 1728-1741.

Parker et al., "Hypothesis for the mechanism of action of ECAP-controlled closed-loop systems for spinal cord stimulation," Healthcare Technology Letters, vol. 7, Iss. 3, doi: 10.1049/htl.2019.0110, May 15, 2020, pp. 76-80.

Wagner et al., "Targeted neurotechnology restores walking in humans with spinal cord injury," Springer, Nature, vol. 536, doi.org/10.1038/s41586-018-0649-2, Nov. 1, 2018, pp. 65-71.

* cited by examiner

100

160

105

120

140

130B

130A

110

EXTERNAL
PROGRAMMER
150

300

510 — DELIVER CONTROL PULSE DISTAL TO SCI

520 — SENSE ECAP SIGNAL

530 — IDENTIFY ECAP CHARACTERISTICS

540 — DETERMINE THERAPY PARAMETER VALUES

550 — DELIVER INFORMED PULSE

SPINAL CORD INJURY THERAPY BASED ON EVOKED COMPOUND ACTION POTENTIALS

This application claims the benefit of U.S. Provisional Patent Application No. 63/231,498, filed Aug. 10, 2021, the entire contents of which is incorporated herein by reference.

TECHNICAL FIELD

This disclosure generally relates to stimulation therapy, and more specifically, control of electrical stimulation therapy for spinal cord injury therapy.

BACKGROUND

Medical devices may be external or implanted and may be used to deliver electrical stimulation therapy to patients via various tissue sites to treat a variety of symptoms or conditions such as chronic pain, dysautonomia, motor deficit, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as "spinal cord stimulation" (SCS), "sacral neuromodulation" (SNM), "deep-brain stimulation" (DBS), and "peripheral-nerve stimulation" (PNS), respectively.

Electrical stimulation therapy may be delivered by the medical device in a "train" of electrical stimulation pulses, and parameters that define the electrical stimulation pulses may include a frequency, an amplitude, a pulse width, and a pulse shape.

SUMMARY

Systems, devices, and techniques are described for controlling electrical stimulation therapy for treatment of one or more conditions associated with a spinal cord injury (SCI) of a patient. In particular, the techniques described herein include sensing an evoked compound action potential (ECAP) and using the ECAP to control spinal cord stimulation (SCS) therapy. In some examples, the system may apply SCS via electrode combination(s) operatively coupled to the patient, including at least one electrode that is positioned distally to (e.g., caudally of) a known location of the patient's SCI.

Stimulation pulses may be configured to provide therapy to treat one or more conditions associated with the patient's SCI. For instance, the stimulation pulses may be configured to enhance a movement, standing, and/or locomotion of the patient. In some such examples, the SCS therapy may be specifically configured to enhance movement and/or strength in the hands and/or arms of the patient. In other examples, the stimulation therapy may be configured to reduce the patient's spasticity. In other examples, the therapy may be configured to help regulate the patient's blood pressure or body temperature, or to enhance the patient's sexual response, or bladder and/or bowel control.

A medical device (e.g., an implantable medical device) may sense an ECAP signal elicited by a stimulation pulse. As described herein, that stimulation pulse may or may not be configured to contribute to a therapeutic effect for the patient. In response to determining that a characteristic of the ECAP signal (e.g., a voltage amplitude) has deviated from a target ECAP characteristic, the system may change one or more stimulation parameters of the next one or more stimulation pulses to be delivered to the patient. For example, the system may increase or decrease a current amplitude of the stimulation pulses by a predetermined step size or based on a gain value representative of a growth curve for the patient. In this manner, the system may be configured to maintain a consistent volume of neural activation by adjusting the one or more stimulation parameters of the stimulation pulses. In other examples, the system may turn stimulation on or off in response to the detected ECAP signal or characteristic of the ECAP signal. In some examples, the system may adjust and synchronize therapy parameter values based on signals obtained from other sensors (e.g., accelerometers, electromyogram sensors, etc.) in addition to the ECAP signals.

In one example, a method includes: delivering, via a first electrode combination, a first stimulation pulse to a portion of a spinal cord of a patient located caudally of a spinal cord injury location of the spinal cord of the patient; sensing, via a second electrode combination, an evoked compound action potential (ECAP) signal elicited by the first stimulation pulse; identifying, by processing circuitry, a characteristic of the ECAP signal; determining, by the processing circuitry and based on the characteristic of the ECAP signal, a therapy parameter value that at least partially defines a second stimulation pulse; and delivering the second stimulation pulse according to the determined therapy parameter value.

In another example, an electrical stimulation therapy system is configured to: deliver, via a first electrode combination, a first stimulation pulse to a portion of a spinal cord of a patient located caudally of a spinal cord injury location of the spinal cord of the patient; sense, via a second electrode combination, an evoked compound action potential (ECAP) signal elicited by the first stimulation pulse; identify, by processing circuitry, a characteristic of the ECAP signal; determine, by the processing circuitry and based on the characteristic of the ECAP signal, a therapy parameter value that at least partially defines a second stimulation pulse; and deliver the second stimulation pulse according to the determined therapy parameter value.

In another example, a computer-readable storage medium comprising instructions that, when executed, cause one or more processors causes processing circuitry to: control delivery, via a first electrode combination, a first stimulation pulse to a portion of a spinal cord of a patient located caudally of a spinal cord injury location of the spinal cord of the patient; sense an evoked compound action potential (ECAP) signal elicited by the first stimulation pulse; identify a characteristic of the ECAP signal; determine, based on the characteristic of the ECAP signal, a therapy parameter value that at least partially defines a second stimulation pulse; and control delivery of the second stimulation pulse according to the determined therapy parameter value.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
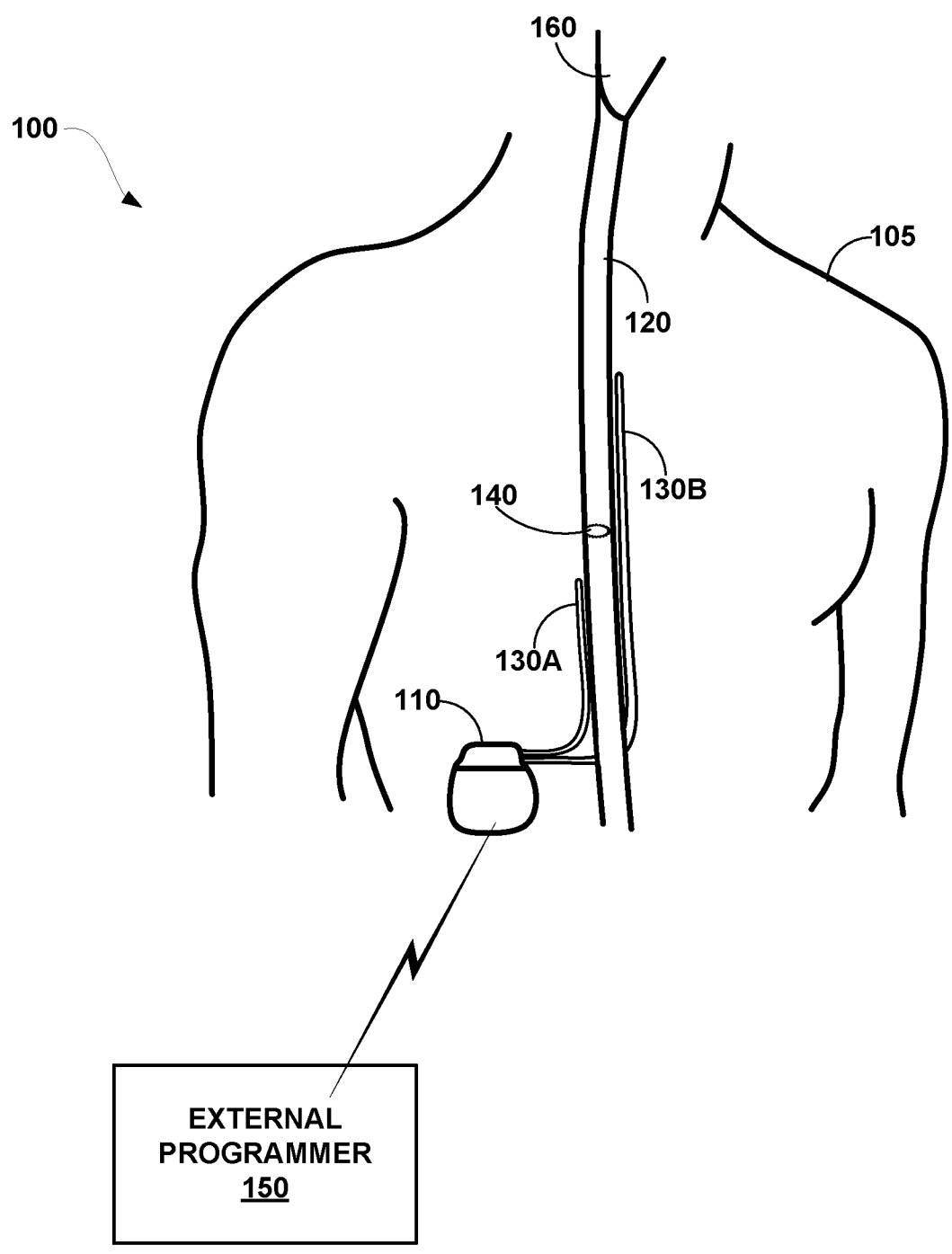
FIG. 1 is a conceptual diagram illustrating an example system that includes a medical device programmer and an implantable medical device (IMD) configured to deliver spinal cord stimulation (SCS) therapy to a patient with a spinal cord injury (SCI).

The disclosure describes examples of medical devices, systems, and techniques for automatically adjusting spinal cord stimulation (SCS) therapy delivered to a patient based on one or more characteristics of evoked compound action potentials (ECAPs) received by a medical device in response to stimulation pulses delivered by the medical device. In some cases, a patient suffering from a spinal cord injury (SCI) may receive SCS therapy for the treatment of pain associated with the SCI. However, other SCI-based conditions, such as bladder and bowel control, general locomotion, or thermal regulation, present a unique problem for more-typical applications of SCS therapy. Specifically, the application of SCS therapy for treatment of many SCI-based conditions often lacks a consistent and reliable feedback mechanism to inform the real-time adjustment of therapy parameters, as needed, to effectively treat the condition.

As described herein, a medical device may be configured to deliver electrical stimulation, which may include a plurality of electrical stimulation pulses, configured to treat one or more conditions associated with the patient's spinal cord injury (SCI) based on one or more characteristics of ECAP signals elicited by previously delivered control pulses. These ECAP signal characteristics can indicate a patient's physiologic state that could benefit from a change in stimulation therapy. Accordingly, the medical device, in some cases, may deliver a plurality of informed pulses, which are configured to provide, or at least contribute to, treatment of the one or more SCI conditions based on one or more characteristics of ECAP signals elicited by control pulses.

In some examples herein, an SCS system may deliver, via an electrode combination, a control stimulation pulse to a dorsal portion of a spinal cord of a patient, wherein the electrode combination is positioned caudally of a spinal cord injury of the patient. For instance, the SCS system may include one or more electrical leads comprising the electrode combination, wherein at least one of the leads is positioned "below" the location of the spinal cord injury, relative to the patient's brain when the patient is in an upright position.

The SCS system may then sense, via the same or a different electrode combination, an evoked compound action potential (ECAP) signal elicited by the control stimulation pulse. The system may identify at least one characteristic (e.g., may measure at least one ECAP parameter value) of the sensed ECAP signal. Various non-limiting examples of identifiable characteristics of ECAP signals include a signal amplitude, a signal width, a signal latency (e.g., a duration between delivery of the control pulse and sensing of the ECAP signal), a signal slope, an area-under-the-curve (AUC) of an ECAP signal, a signal phasing, a signal curvature, an oscillatory signal pattern, a signal morphology; or a temporal stability or temporal variance of an ECAP signal.

In response to identifying at least one ECAP characteristic, the SCS system may determine a therapy parameter value that at least partially defines an "informed" or "therapeutic" stimulation pulse or pulses configured to treat a patient condition. As used herein, a "therapy" or "treatment" of a patient condition associated with an SCI may refer to an electrical-stimulation-based enhancement of a bodily movement or function of the patient that has been limited or prevented by damage to the patient's spinal cord. For instance, the informed stimulation pulses may be configured to enhance a general movement, standing, and/or locomotion of the patient. In some such examples, the SCS therapy may be specifically configured to enhance movement and/or strength in the hands, feet, arms and/or legs of the patient. In other examples, the stimulation therapy may be configured to reduce muscle spasms, or "spasticity," resulting from the SCI. In other examples, the SCS therapy may be configured to help regulate the patient's blood pressure or body temperature, or to enhance a sexual response, or to improve the patient's bladder and/or bowel control. These examples are merely illustrative, and the techniques described herein may be applied similarly for the treatment of any amenable condition resulting from, or otherwise associated with, a spinal cord injury.

In some of the examples described herein, the "informed" stimulation pulse(s) (e.g., the one or more "therapeutic" pulse(s)) may be configured to induce a "macro-function" of the patient. For instance, the stimulation therapy may be configured to enable and/or enhance the natural ability of the patient's spinal cord to execute a complex bodily movement or function, e.g., involving more than one muscle and/or distinct movements thereof. In some such examples, the SCS system may iteratively modify (e.g., determine and deliver) informed stimulation pulses based on identified ECAP characteristics in order to guide a complete "start to finish" bodily motion or function of the patient. Equally as importantly, in some examples, the SCS system may be configured to determine, based on the sensed ECAP signals, a precise time at which to disable the stimulation therapy (e.g., to terminate delivery of informed stimulation pulses) to allow the patient's spinal cord to execute the macro-function without further interference from delivered electrical stimulation.

In some examples, the control stimulation pulses may be defined by one or more stimulation parameters, other than just amplitude, different than the informed stimulation pulses. For example, the control stimulation pulses may be defined by a different pulse width, frequency, electrode combination, etc. These different stimulation parameters of the control stimulation pulses may enable the system to elicit detectable ECAP signals that can be used to adjust the informed stimulation pulses configured to provide therapy to the patient. In situations where the control stimulation pulses themselves can contribute to therapy, the system may only deliver control stimulation pulses and adjust a parameter, such as amplitude, of subsequent control stimulation pulses based on the ECAP signal elicited by a prior control stimulation pulse. In some examples, a system may deliver one or more informed pulses between respective control pulses in order to provide therapy and sense ECAP signals during the therapy regime. In this manner, a train of informed pulses may be at least partially interleaved with a train of control pulses. The informed and control pulses may alternate every pulse on a 1:1 bases, multiple informed pulses may be delivered between each control pulse, or multiple control pulses may be delivered between each informed pulse. The system may adjust the ratio of informed pulses to control pulses over time as needed to maintain therapy and/or sense ECAP signals at a sufficient frequency to provide feedback for the informed pulses.

In some examples, the SCS systems described herein may be configured to provide different types of SCS therapy in different scenarios, e.g., in response to different inputs or conditions. For instance, the SCS system may be configured to determine, based on identified "signature" ECAP characteristics, a "volitional intent" of the patient, or in other words, an intended bodily movement or intended bodily function of the patient. In examples in which the patient intends to execute a bodily movement, the volitional intent may be referred to as a "locomotor intent." In response, the SCS system may select an appropriate stimulation therapy program from among a plurality of therapy programs stored in memory to enable or enhance the intended movement or function. In some examples, the SCS system is configured to identify or assess long-term trends across sensed ECAP signals stored in memory, e.g., to monitor recovery of the patient's spinal cord. Additionally or alternatively, the SCS system may determine, based on the one or more identified ECAP characteristics, an underlying neurophysiologic state of the patient, which the SCS system may similarly be configured to monitor over time to inform treatments.

In some examples, but not all examples, the system may include two or more distinct electrode leads, including a first lead comprising a first electrode combination positioned caudally of the SCI location, and a second lead comprising a second electrode combination. The second lead may be positioned either cranially of the spinal cord injury, or caudally of the spinal cord injury. In some such examples, the system may compare first ECAP signals sensed by the first electrode combination to second ECAPs signals sensed by the second electrode combination, to further inform and improve the determination of appropriate therapy parameter values.

In some examples, the SCS system may further include one or more additional types of sensors, such as an accelerometer, an electroencephalogram (EEG) sensor, an electromyogram (EMG) sensor, or the like, configured to generate sensor data indicating a condition associated with the patient or with an environment in which the patient is located. In some such examples, the SCS system may be configured to determine therapy parameter values based on both the identified characteristic of the ECAP signal and on the additional sensor data.

In some examples, the SCS system may be configured to "sample" (e.g., sense) an ECAP signal according to a predetermined sampling frequency, which may correspond to selected stimulation pulses that elicit an ECAP or a frequency of control stimulation pulses. As one non-limiting example, the predetermined sampling frequency may be from about 1 Hz to about 100 Hz, or about 50 Hz in one example.

In some examples, but not all examples, in the control stimulation pulse may be configured to at least partially contribute to the therapy (e.g., elicit a therapeutic response) provided to the patient, e.g., in addition to eliciting the ECAP signal. In other examples, the control stimulation pulse may only be configured to elicit the ECAP signal, e.g., without contributing to a therapeutic effect for the patient.

In some examples in accordance with this disclosure, an SCS system is configured to apply one or more machine-learning models or algorithms trained to dynamically control the delivery of SCS therapy over time. For instance, the SCS system may be configured to iteratively vary therapy parameter values of control pulses until a desired patient condition is detected, e.g., an intended locomotive state, a preferred blood-pressure level, etc. Once the preferred patient condition is detected, the SCS system may capture and store an ECAP "template" indicating a detected ECAP signal at the time of the detected desired patient response. The SCS system, e.g., via one or more machine-learning algorithms, may then continue to vary the therapy parameter values to maintain the template ECAP response, e.g., as a proxy for maintaining the desired patient condition. In other words, the machine-learning algorithm may be trained to recognize "good" or "desired" ECAP characteristics, as well as "bad" or "undesired" ECAP characteristics, within sensed ECAP signals. Accordingly, when the machine-learning algorithm identifies an undesired ECAP characteristic, the SCS system may then modify one or more therapy parameter values to attempt to reduce the undesired ECAP characteristic and maintain or induce desired ECAP characteristics.

As a further example, the SCS system may use stored ECAP templates (e.g., indicating preferred ranges of sensed ECAP characteristics) to determine whether delivered stimulation is "appropriate." For instance, an identified out-of-range ECAP characteristic indicate that the delivered stimulation therapy is not appropriate, due to incorrect placement of the leads resulting from lead migration or other similar anomalies. In such examples, the SCS system may iteratively vary the therapy parameter values (e.g., including the particular electrode combination delivering the therapy pulses) until a preferred ECAP response is regained, or, in some examples, may output an alert requesting that lead placement be corrected.

Although SCS is generally described herein in the form of electrical stimulation "pulses," SCS may be delivered in non-pulse form in other examples. For example, SCS may be delivered as a signal having various waveform shapes, frequencies, and amplitudes. Therefore, electrical stimulation in the form of a non-pulse signal may be a continuous signal than may have a sinusoidal waveform or other continuous waveform.

FIG. 1 is a conceptual diagram illustrating an example spinal-cord-stimulation (SCS) system 100 that includes implantable medical device (IMD) 110 configured to deliver electrical stimulation therapy, and in particular, SCS therapy, to a patient 105 afflicted with a spinal cord injury (SCI) 140. Although the techniques described in this disclosure are generally applicable to a variety of medical devices including external (e.g., epidural) and implantable medical devices (IMDs), application of such techniques to IMDs and, more particularly, implantable electrical stimulators (e.g., neurostimulators) will be described for purposes of illustration.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of electrodes of leads 130A and/or 130B (collectively, "leads 130," or in the alternative, "lead 130"), e.g., for treatment of one or more conditions resulting directly from, or otherwise associated with, the patient's SCI 140. In other examples, IMD 110 may be coupled to a single lead 130 carrying multiple electrodes or more than two leads each carrying multiple electrodes. In addition to electrical stimulation therapy, IMD 110 may also be configured to generate and deliver "control" stimulation pulses configured to elicit ECAP signals that may or may not contribute to the therapy provided by "informed" stimulation pulses. As discussed herein, the control pulses may be non-therapeutic in some examples. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In other examples, leads 130 are positioned externally to the patient's epidermis. In some examples, IMD 110 uses one or more leads 130, while in other examples, IMD 110 is leadless.

IMD 110 may be constructed of any polymer, metal, or composite material sufficient to house the components of IMD 110 (e.g., components illustrated in FIG. 2A) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks, or other suitable site within patient 105. The outer housing of IMD 110 may be configured to provide a hermetic seal for components, such as a rechargeable or non-rechargeable power source. In addition, in some examples, the outer housing of IMD 110 may be selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator in IMD 110 to tissue of patient 105.

In accordance with techniques of this disclosure, SCS system 100 includes at least one implantable lead 130 (depicted in FIG. 1 as lead 130A) that is positioned on an opposite or "caudal" side of spinal cord injury 140 relative to the patient's brain 160, and on a "dorsal" (e.g., back) side of spinal cord 120. In the example depicted in FIG. 1, lead 130A is positioned on the distal side of SCI 140, and lead 130B is positioned on a same (or "cranial") side of SCI 140 as the patient's brain 160. In some such examples, SCS system 100 may compare first signals sensed by the electrodes of lead 130A to second signals sensed by the electrodes of lead 130B, to inform and improve the determination of appropriate stimulation therapy parameters. In other examples, both of leads 130 may be positioned caudally of SCI 140.

Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead 130 or more than two leads 130, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, and voltage or current amplitude, pulse frequency, pulse width, or pulse shape of stimulation delivered by the electrodes. These stimulation parameters of informed pulses are typically predetermined parameter values determined prior to delivery of the informed pulses. However, in some examples, system 100 may change one or more parameter values automatically based on one or more factors or based on user input.

In addition to stimulation informed pulses, an ECAP "test" stimulation program may define stimulation parameter values that define control pulses delivered by IMD 110 through at least some of the electrodes of leads 130. These stimulation parameter values may include information identifying which electrodes have been selected for delivery of control pulses, the polarities of the selected electrodes, i.e., the electrode combination for the program, and voltage or current amplitude, pulse frequency, pulse width, and pulse shape of stimulation delivered by the electrodes. The stimulation signals (e.g., one or more stimulation pulses or a continuous stimulation waveform) defined by the parameters of each ECAP test stimulation program are configured to evoke a compound action potential from nerves. In some examples, the ECAP test stimulation program may define when the control pulses are to be delivered to the patient based on the frequency and/or pulse width of the informed pulses. However, the stimulation defined by each ECAP test stimulation program are not intended to provide or contribute to therapy for the patient. In an example where the control pulses contribute to or provide therapy for the patient, the ECAP test stimulation program may also be used in place of, or be the same as, a therapy stimulation program.

SCS system 100 is directed to SCS therapy, e.g., used to treat one or more conditions associated with SCI 140. For instance, the informed stimulation pulses of the SCS therapy may be configured to, as non-limiting examples, enhance a general movement, standing, and/or locomotion of the patient; enhance movement and/or strength in the hands, feet, arms and/or legs of the patient; reduce pain or spasticity resulting from the SCI; regulate the patient's blood pressure and/or body temperature; enhance a sexual response; or to improve the patient's bladder and/or bowel control. These examples are merely illustrative, and the techniques described herein may be applied similarly for the treatment of any amenable condition resulting from or otherwise associated with a SCI 140.

In some examples, IMD 110 (e.g., lead 130) may include one or more sensors configured to allow IMD 110 to monitor one or more parameters of patient 105, such as patient activity, pressure, temperature, movement, or other characteristics. As non-limiting examples, sensors of IMD 110 may include accelerometer(s), EEG(s), EMG(s), or the like. The one or more sensors may be provided in addition to, or in place of, therapy delivery by lead 130.

IMD 110 is configured to deliver SCS therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical or lumbar regions.

Stimulation of spinal cord 120 may, for example, induce a desired "macro-function." For instance, research indicates that the spinal cord is capable of executing complex bodily movements or functions, e.g., involving multiple muscles or organs and/or multiple individual movements or functions thereof, by actuating specific combinations of nerve fibers, as compared to sequentially actuating each individual nerve fiber or subset of nerve fibers required to complete the motion. As one illustrative example, while raising the patient's arm above the head requires just one initial "command" from the patient's brain 160, the actual execution of the movement involves a fairly complex interaction of muscle contractions, including of the trapezius, deltoid, and triceps muscles, controlled by spinal cord 120. As detailed further below, the targeted, ECAP-informed stimulation of spinal cord 120 can help restore macro-functionality, such as standing, walking, bladder and bowel control, etc., that is otherwise impaired by spinal cord injury 140.

In other examples, stimulation of spinal cord 120 may prevent pain signals from traveling through spinal cord 120 and to the brain 160 of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

IMD 110 generates and delivers electrical stimulation therapy to a target stimulation site within patient 105 via the electrodes of leads 130 to patient 105 according to one or more therapy stimulation programs. A therapy stimulation program defines values for one or more parameters that define an aspect of the therapy delivered by IMD 110 according to that program. For example, a therapy stimulation program that controls delivery of stimulation by IMD 110 in the form of pulses may define values for voltage or current pulse amplitude, pulse width, and pulse rate (e.g., pulse frequency) for stimulation pulses delivered by IMD 110 according to that program. A therapy stimulation program may define control pulses and/or informed pulses when these pulses are configured to contribute to the therapeutic effect (e.g., paresthesia, pain blocking, etc.) for the patient.

Furthermore, IMD 110 is configured to deliver control stimulation to patient 105 via a combination of electrodes of leads 130, alone or in combination with an electrode carried by or defined by an outer housing of IMD 110. The tissue targeted by the control stimulation may be the same tissue targeted by the electrical stimulation therapy, but IMD 110 may deliver control pulses via the same, at least some of the same, or different electrodes, and intended to elicit a detectable ECAP signal. This control stimulation may (e.g., therapeutic stimulation) or may not (e.g., non-therapeutic stimulation) contribute to a therapeutic effect for the patient. Since control pulses can be delivered in an interleaved manner with informed pulses, a clinician and/or user may select any desired electrode combination for informed pulses. Like the electrical stimulation therapy, the control stimulation may be in the form of electrical stimulation pulses or continuous waveforms.

In one example, each control pulse may include a balanced, bi-phasic square pulse that employs an active recharge phase. However, in other examples, the control pulses may include a monophasic pulse followed by a passive recharge phase. In other examples, a control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. The control pulses may elicit an ECAP signal from the tissue, and IMD 110 may sense the ECAP signal via two or more electrodes on leads 130. In cases where the control pulses are applied to spinal cord 120, the signal may be sensed by IMD 110 from spinal cord 120. As discussed herein, the control stimulation may contribute, alone or in part, to the therapeutic effect received by the patient. In other words, control pulses may be delivered to provide therapy without any additional informed pulses in some examples. In examples in which the control pulses alone can provide therapy to the patient, the control stimulation may be the therapy stimulation for that patient.

In some examples, but not all examples, IMD 110 may deliver control stimulation to a target stimulation site within patient 105 via the electrodes of leads 130 according to one or more ECAP test stimulation programs. The one or more ECAP test stimulation programs may be stored in a memory of IMD 110. Each ECAP test program of the one or more ECAP test stimulation programs includes values for one or more parameters that define an aspect of the control stimulation delivered by IMD 110 according to that program, such as current or voltage amplitude, pulse width, pulse frequency, electrode combination, and, in some examples, timing based on informed pulses to be delivered to patient 105. In some examples, IMD 110 delivers control stimulation to patient 105 according to multiple ECAP test stimulation programs.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from programmer 150 to control electrical stimulation therapy (e.g., informed pulses, and in some examples control pulses) and control stimulation (e.g., control pulses). For example, external programmer 150 may transmit therapy stimulation programs, ECAP test stimulation programs, stimulation parameter adjustments, therapy stimulation program selections, ECAP test program selections, user input, or other information to control the operation of IMD 110, e.g., by wireless telemetry or wired connection.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and programmer 150 may communicate via wireless communication using any techniques known in the art. Examples of communication techniques may include, for example, radiofrequency (RF) telemetry and inductive coupling, but other techniques are also contemplated. In some examples, programmer 150 may include a communication head that may be placed proximate to the patient's body near the IMD 110 implant site to improve the quality or security of communication between IMD 110 and programmer 150. Communication between programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 may modify therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

In this disclosure, efficacy of SCS therapy may be indicated by one or more characteristics of an action potential that is evoked by a stimulation pulse delivered by IMD 110 (i.e., a characteristic of the ECAP signal). Various non-limiting examples of identifiable characteristics of ECAP signals include a signal amplitude (e.g., an amplitude of or between one or more signal peaks), a signal width, a signal latency (e.g., a duration between delivery of the control pulse and sensing of the ECAP signal), a signal slope, an area-under-the-curve (AUC) of one or more peaks, a signal phasing, a signal curvature, an oscillatory signal pattern, a signal morphology; or a temporal stability or temporal variance of the ECAP signal.

In some examples, IMD 110 is configured to measure or sense the ECAP signal on a substantially continuous basis, e.g., in examples in which the stimulation therapy includes a generally continuous waveform rather than a discrete pulse train. In other examples, IMD 110 is configured to measure or sense the ECAP signal in response to the delivery of each informed stimulation pulse. In other examples, IMD 110 is configured to "sample" the ECAP signal at a predetermined sampling frequency, such as about 50 Hz, as one non-limiting example.

Electrical-stimulation-therapy delivery by leads 130 of IMD 110 may cause neurons within the target tissue to evoke a compound action potential that travels up and down the target tissue, eventually arriving at sensing electrodes of IMD 110. Furthermore, control stimulation may also elicit at least one ECAP, and ECAPs responsive to control stimulation may also be a surrogate for the effectiveness of the therapy. The number of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse. In some examples, these parameters may contribute to an intensity of the electrical stimulation. In addition, a characteristic of the ECAP signal (e.g., an amplitude) may change based on the distance between the stimulation electrodes and the nerves subject to the electrical field produced by the delivered control pulses.

In one example, each informed pulse may have a pulse width greater than approximately 300 μs, such as between approximately 300 μs and 1000 μs (i.e., 1 millisecond) in some examples. At these pulse widths, IMD 110 may not sufficiently detect an ECAP signal because the informed pulse is also detected as an artifact that obscures the ECAP signal. If ECAPs are not adequately recorded, then ECAPs arriving at IMD 110 cannot be compared to the target ECAP characteristic (e.g. a target ECAP amplitude), and electrical therapy stimulation cannot be altered according to responsive ECAPs. When informed pulses have these longer pulse widths, IMD 110 may deliver control stimulation in the form of control pulses. The control pulses may have pulse widths of less than approximately 300 μs, such as a bi-phasic pulse with each phase having a duration of approximately 100 μs. Since the control pulses may have shorter pulse widths than the informed pulses, the ECAP signal may be sensed and identified following each control pulse and used to inform IMD 110 about any changes that should be made to the informed pulses (and control pulses in some examples). In some examples, at least some informed pulses may have pulse widths less than approximately 300 μs. In such examples, control pulses interleaved with the informed pulses may have pulse widths shorter than the pulse widths of informed pulses. In other examples, a control pulse may have a pulse width greater than the pulse width of the informed pulse. In general, the term "pulse width" refers to the collective duration of every phase, and interphase interval when appropriate, of a single pulse. A single pulse may include a single phase in some examples (i.e., a monophasic pulse) or two or more phases in other examples (e.g., a bi-phasic pulse or a tri-phasic pulse). The pulse width defines a period of time beginning with a start time of a first phase of the pulse and concluding with an end time of a last phase of the pulse (e.g., a biphasic pulse having a positive phase lasting 100 μs, a negative phase lasting 100 μs, and an interphase interval lasting 30 μs defines a pulse width of 230 μs). In some examples, the informed pulses may consist of a train of multiple consecutive pulses with a parameter set (pulse width, amplitude, pulse-to-pulse period, morphology) informed by a preceding control pulse. In other words, in some cases, a plurality of consecutive informed pulses may be interleaved between a pair of discrete control pulses. In this manner, one or more informed pulses may be delivered between each control pulse of a train of control pulses. The system may adjust this ratio of informed pulses to control pulses as needed, e.g., in response to one or more factors associated with therapy, ECAP sensing, and/or system characteristics such as battery life (e.g., fewer delivered pulses increases battery life).

As described, the example techniques for adjusting stimulation parameter values for informed pulses are based on comparing the value of a characteristic of a measured ECAP signal to a target ECAP characteristic value. During delivery of control pulses defined by one or more ECAP test stimulation programs, IMD 110, via two or more electrodes interposed on leads 130, senses electrical potentials of tissue of the spinal cord 120 of patient 105 to measure the electrical activity of the tissue. IMD 110 senses ECAPs from the target tissue of patient 105, e.g., with electrodes on one or more leads 130 and associated sense circuitry. In some examples, IMD 110 receives a signal indicative of the ECAP from one or more sensors, e.g., one or more electrodes and circuitry, internal or external to patient 105. Such an example signal may include a signal indicating an ECAP of the tissue of the patient 105. Examples of the one or more sensors include one or more sensors configured to measure a compound action potential of the patient 105, or a physiological effect indicative of a compound action potential. For example, to measure a physiological effect of a compound action potential, the one or more sensors may be an accelerometer, a pressure sensor, a bending sensor, a sensor configured to detect a posture of patient 105, or a sensor configured to detect a respiratory function of patient 105. However, in other examples, external programmer 150 receives a signal indicating a compound action potential in the target tissue of patient 105 and transmits a notification to IMD 110.

In the example of FIG. 1, IMD 110 described as performing a plurality of processing and computing functions. However, external programmer 150 instead may perform one, several, or all of these functions. In this alternative example, IMD 110 functions to relay sensed signals to external programmer 150 for analysis, and external programmer 150 transmits instructions to IMD 110 to adjust the one or more parameters defining the electrical stimulation therapy based on analysis of the sensed signals. For example, IMD 110 may relay the sensed signal indicative of an ECAP to external programmer 150. External programmer 150 may compare the parameter value of the ECAP to the target ECAP characteristic value, and in response to the comparison, external programmer 150 may instruct IMD 110 to adjust one or more parameter that defines the electrical stimulation informed pulses and, in some examples, control pulses, delivered to patient 105.

In the example techniques described in this disclosure, the control stimulation parameters and the target ECAP characteristic values may be initially set at the clinic but may be set and/or adjusted at home by patient 105. Once the target ECAP characteristic values are set, the example techniques allow for automatic adjustment of informed pulse parameters to maintain consistent volume of neural activation and consistent perception of therapy for the patient when the electrode-to-neuron distance changes. The ability to change the stimulation parameter values may also allow the therapy to have long term efficacy, with the ability to keep the intensity of the stimulation (e.g., as indicated by the ECAP) consistent by comparing the measured ECAP values to the target ECAP characteristic value. IMD 110 may perform these changes without intervention by a physician or patient 105.

In some examples, SCS system 100 may change the target ECAP characteristic value over a period of time. SCS system 100 may be programmed to change the target ECAP characteristic in order to adjust the intensity of informed pulses, e.g., to induce different bodily movements or functions, or to provide varying sensations to the patient (e.g., increase or decrease the volume of neural activation). In one example, SCS system 100 may be programmed to oscillate a target ECAP characteristic value between a maximum target ECAP characteristic value and a minimum target ECAP characteristic value at a predetermined frequency to provide a sensation to the patient that may be perceived as a wave or other sensation that may provide therapeutic relief for the patient. The maximum target ECAP characteristic value, the minimum target ECAP characteristic value, and the predetermined frequency may be stored in the memory of IMD 110 and may be updated in response to a signal from external programmer 150 (e.g., a user request to change the values stored in the memory of IMD 110). In other examples, the target ECAP characteristic value may be programed to steadily increase or steadily decrease to a baseline target ECAP characteristic value over a period of time. In other examples, external programmer 150 may program the target ECAP characteristic value to automatically change over time according to other predetermined functions or patterns. In other words, the target ECAP characteristic value may be programmed to change incrementally by a predetermined amount or predetermined percentage, the predetermined amount or percentage being selected according to a predetermined function (e.g., sinusoid function, ramp function, exponential function, logarithmic function, or the like). Increments in which the target ECAP characteristic value is changed may be changed for every certain number of pulses or a certain unit of time. Although the system may change the target ECAP characteristic value, received ECAP signals may still be used by the system to adjust one or more parameter values of the informed pulses and/or control pulses in order to meet the target ECAP characteristic value.

In some examples, SCS system 100 may be configured to provide different types of stimulation therapy (e.g., produce different therapeutic effects) in response to different inputs or detected conditions. For instance, SCS system 100 may be configured to determine, based on one or more identified characteristics of a sensed ECAP signal, a "volitional intent" of the patient. In other words, a particular signature or pattern within the sensed ECAP signal may indicate an intended movement (e.g., a locomotor intent) or bodily function of the patient, such as standing, walking, urination, etc. In response to identifying such a signature (e.g., by comparing sensed ECAP parameters to values stored in memory), IMD 110 may select an appropriate therapy stimulation program to enable or enhance the intended locomotion.

In some examples, SCS system 100 is configured to periodically store sensed ECAP signal parameters in memory. SCS system 100 may use the stored ECAP parameters to monitor a neurophysiologic state of the patient over time, e.g., to enable long-term monitoring of the healing of SCI 140.

In some examples in accordance with this disclosure, SCS system 100 includes at least one computing device (e.g., processing circuitry of IMD 110 and/or external programmer 150) configured to apply one or more machine-learning models or algorithms trained to dynamically control the SCS therapy over time. For instance, SCS system 100 may be configured to iteratively vary therapy parameter values of control pulses until a desired patient condition is elicited, such as a locomotive state (e.g., standing, walking), a preferred blood-pressure level, etc. Once the desired patient condition is detected, SCS system 100 may capture and store an ECAP response "template" indicating a sensed ECAP signal at the time of the elicited patient condition. SCS system 100, e.g., via one or more machine-learning algorithms, may then continue to vary the therapy parameter values, as necessary, to maintain a sensed ECAP signal consistent with the ECAP template.

In further examples, SCS system 100 may be configured to used stored ECAP templates to determine whether present SCS therapy levels are "appropriate." For instance, due to undesired migration of lead(s) 130 or other similar factors, SCS system 100 may determine that certain identified ECAP characteristics are outside a maximum-allowable variance from stored template values. In such examples, SCS system 110 may iteratively vary therapy parameter values until ECAP signals consistent with the preferred response template are regained, and/or may output an alert requesting manual correction.

Figure 2A:
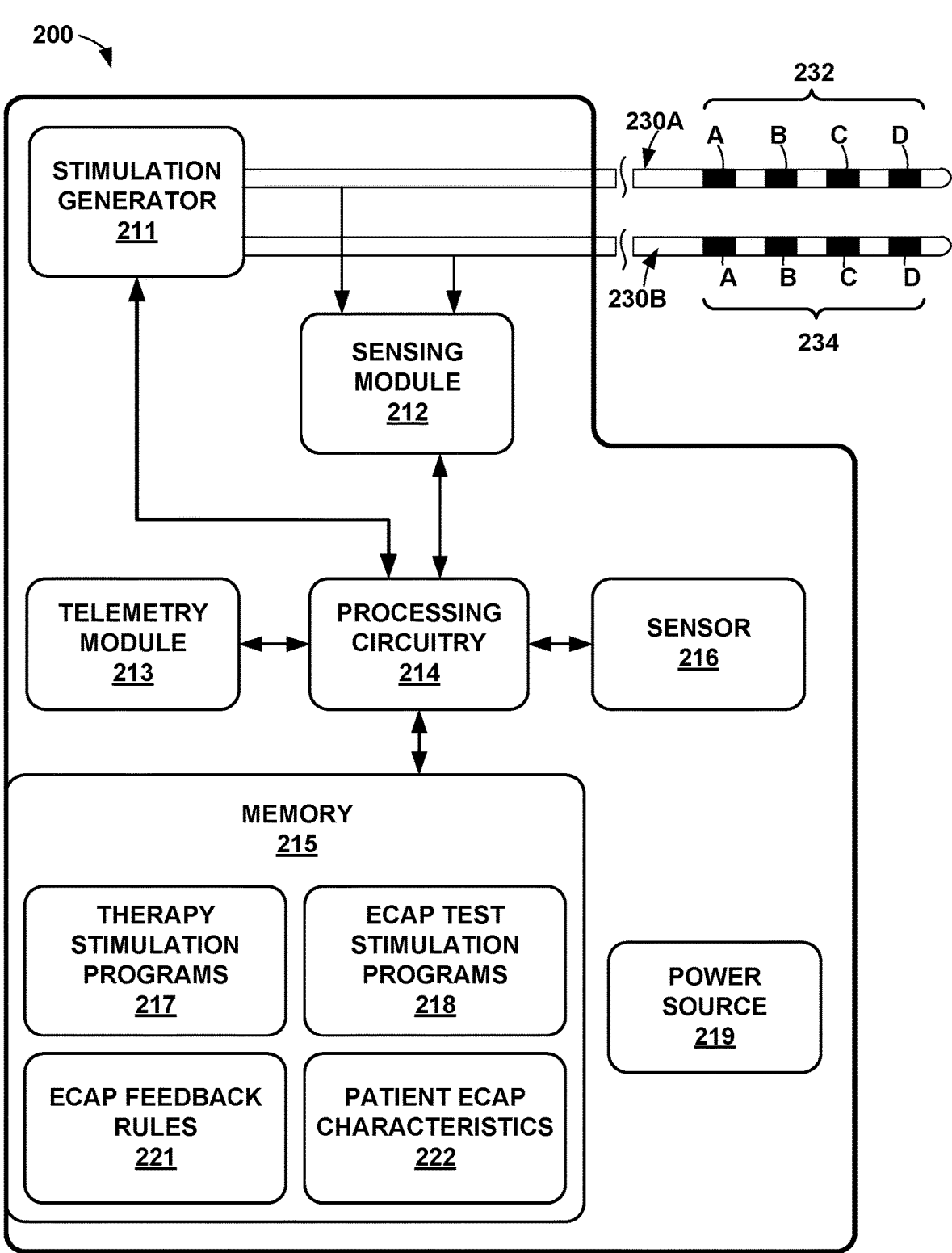
FIG. 2A is a block diagram illustrating some example components of the IMD of FIG. 1.

FIG. 2A is a block diagram illustrating some example components of an IMD 200, which is an example of IMD 110 of FIG. 1. In the example shown in FIG. 2A, IMD 200 includes processing circuitry 214, memory 215, stimulation generator 211, sensing module 212, telemetry module 213, sensor 216, and power source 219. Each of these modules may be or may include programmable or fixed-function circuitry configured to perform the functions attributed to respective circuitry. For example, processing circuitry 214 may include fixed-function or programmable circuitry; stimulation generator 211 may include circuitry configured to generate stimulation signals such as pulses or continuous waveforms on one or more channels; sensing module 212 may include sensing circuitry for sensing signals, and telemetry module 213 may include telemetry circuitry for transmission and reception of signals. Memory 215 may store computer-readable instructions that, when executed by processing circuitry 214, cause IMD 200 to perform various functions described herein. Memory 215 may be a storage device or other non-transitory medium.

In the example shown in FIG. 2A, memory 215 stores therapy stimulation programs 217 and ECAP test stimulation programs 218 in separate (e.g., physically distinct) memories within memory 215 or separate areas (e.g., partitions) within memory 215. Memory 215 also stores target ECAP feedback rules 221 and patient ECAP characteristics 222. Each stored therapy stimulation program 217 defines values for a set of electrical stimulation parameters (e.g., a parameter set or set of parameter values), such as a stimulation electrode combination, electrode polarity, current or voltage amplitude, pulse width, pulse rate, and pulse shape. Each of stored ECAP test stimulation programs 218 defines values for a corresponding set of electrical stimulation parameters (e.g., a control stimulation parameter set), such as a stimulation electrode combination, electrode polarity, current or voltage amplitude, pulse width, pulse rate, and pulse shape. ECAP test stimulation programs 218 may also have additional information such as instructions regarding when to deliver control pulses based on the pulse width and/or frequency of the informed pulses defined in therapy stimulation programs 217.

Accordingly, in some examples, stimulation generator 211 generates electrical stimulation signals in accordance with the electrical stimulation parameters noted above. Other ranges of parameter values may also be useful and may depend on the target stimulation site within patient 105. While stimulation pulses are described, stimulation signals may be of any form, such as time-continuous signals (e.g., sinusoidal waves) or the like.

In some examples, IMD 200 may include independently controllable current sources and sinks coupled to individual electrodes 232, 234. For instance, stimulation generator 211 may include an array of regulated current sources and sinks, coupled (via implantable leads 230) to respective individual electrodes 232, 234, that can be selectively activated to form electrode combinations and deliver stimulation pulses. In some such examples, to interleave control stimulation pulses with informed stimulation pulses, IMD 200 may further include one or more gate transistors to actuate the current sources or sinks and/or to toggle between stimulation generator 211 and sensing module 212.

For example, to activate electrode 232A as a cathode, processing circuitry 214 may turn on a current source (e.g., of stimulation generator 211) that is connected to electrode 232A and specify an amount of electric current amplitude to be delivered with each pulse. To activate electrode 232B as an anode, processing circuitry 214 may turn on a current sink (e.g., of stimulation generator 211) connected to electrode 232B, which causes electrode 232B to sink the amount of current sourced by electrode 232A. IMD 200 can time-mux different electrode combinations by turning on different sources and sinks of stimulation generator 211, connected to other selected electrodes, at different times. IMD 200 can also form multi-electrode combinations of multiple cathodes and/or multiple anodes (or one cathode and multiple anodes or one anode and multiple cathodes) by selectively turning on particular sources and sinks, with the total amount of current sourced by the current sources of the cathodes being equal to the total amount of current sunk by the current sinks of the anode.

In some examples, each current source or sink of stimulation generator 211 may be or may include a set of multiple, parallel sources and sinks formed by branches of a current mirror circuit. IMD 200 may selectively activate the parallel sources and sinks to dial up or down the amount of current for a given electrode 232, 234. For example, if there are 64 parallel source branches, activating 32 of them provides 32 times the current delivered in the reference branch of the current mirror circuit, e.g., 50% of the maximum possible current that could be delivered (e.g., if all 64 branches were activated) by the electrode 232, 234. In some instances, the reference current may also be adjustable. In some examples, the outer housing of IMD 200 may also form an anode for some applications.

Processing circuitry 214 may include any one or more of a microprocessor, a controller, a digital-signal processor (DSP), an application-specific integrated circuit (ASIC), a field-programmable gate array (FPGA), discrete logic circuitry, or any other processing circuitry configured to provide the functions attributed to processing circuitry 214 herein, and may be embodied as firmware, hardware, software, or any combination thereof. Processing circuitry 214 controls stimulation generator 211 to generate stimulation signals according to therapy stimulation programs 217 and ECAP test stimulation programs 218 stored in memory 215 to apply stimulation parameter values specified by one or more of programs, such as amplitude, pulse width, pulse rate, and pulse shape of each of the stimulation signals.

In the example shown in FIG. 2A, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 214 also controls stimulation generator 211 to generate and apply the stimulation signals to selected combinations of electrodes 232, 234. In some examples, stimulation generator 211 includes a switch circuit that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord 120 of the patient 105 (FIG. 1) with selected electrodes 232, 234.

In other examples, however, stimulation generator 211 does not include a switch circuit and, as described above, stimulation generator 211 comprises a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generator 211 via respective wires that are straight or coiled within the housing of the lead 230 and run to a connector at the proximal end of the lead. In another example, each of the electrodes 232, 234 of the lead 230 may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 212 is incorporated into a common housing with stimulation generator 211 and processing circuitry 214 in FIG. 2A, in other examples, sensing circuitry 212 may be in a separate housing from IMD 200 and may communicate with processing circuitry 214 via wired or wireless communication techniques.

In some examples, one or more of electrodes 232 and 234 may be suitable for sensing the ECAPs. For instance, electrodes 232 and 234 may sense the voltage amplitude of a portion of the ECAP signals, where the sensed voltage amplitude is a characteristic the ECAP signal.

Sensor 216 may include one or more sensing elements that sense values of a respective patient parameter. As described, electrodes 232 and 234 may be the electrodes that sense the parameter value of the ECAP. Sensor 216 may include one or more accelerometers, optical sensors, chemical sensors, temperature sensors, pressure sensors, EEG sensors, EMG sensors, or any other types of sensors. Sensor 216 may output patient parameter values that may be used as feedback to control delivery of SCS therapy.

As described herein, in some examples, processing circuitry 214 is configured to "synchronize" the delivery of stimulation pulses to signals received from sensor 216, as informed by sensed ECAP signals, to help contribute to inducement or to enhance a patient bodily function or movement. In other words, processing circuitry 214 is configured to "time" or "gate" the stimulation delivery, not only based on a motor response of the patient (e.g., as indicated by received sensor data), but also based on the patient's neural activity (e.g., based on sensed ECAP signals). The combination of ECAP data and other sensor data in this way provides a number of unique benefits for the treatment of SCI-related conditions. For instance, the use of sensed ECAP signals to inform stimulation therapy may help compensate for one or more disadvantages associated with the use of sensor data alone, e.g., by substantially reducing a latency inherent in more-typical sensor data. As an illustrative example, an accelerometer attached to a limb of patient 105 may be cause a processing latency on the order of 10 milliseconds (ms) to 100 ms before the sensor detects a movement of the patient's limb, processes the information, and transmits an appropriate signal back to processing circuitry 214. Similarly, the use of additional sensor data to inform stimulation therapy may help compensate for one or more disadvantages associated with the use of sensed ECAP signals alone, e.g., by resolving an ambiguous interpretation of a sensed ECAP characteristic, by providing data redundancy in cases of lead migration or other source of low signal-to-noise ratio, or the like. In many examples, lead migration may be associated with a postural variability (e.g., general change in bodily orientation) of patient 105, however, it should be noted that this factor may be less common with SCS systems for SCI patients than with other SCS systems, e.g., due to patient mobility limitations often resulting from spinal cord injuries. Accordingly, processing circuitry 214 is configured to dynamically determine and update therapy parameter values based both on identified characteristics of sensed ECAP signals, as well as received sensor data, in order to treat a patient condition and/or contribute to or complete a bodily function or bodily movement (e.g., a macro-function).

As one non-limiting, illustrative example of the techniques described herein, processing circuitry 214 may determine, based on identified characteristics of sensed ECAP signals, that patient 105 has "expressed" a locomotor intent to move his or her leg in order to take a step (e.g., to stand or walk). In some such examples, processing circuitry 214 may additionally receive data from sensor 216 (e.g., an accelerometer) indicating a current orientation of the patient's stepping leg relative to the ground. In order to help induce and/or complete the patient's step, processing circuitry 214 may be configured to cause stimulation generator 211 to deliver appropriate stimulation pulse(s) that assist patient 105 to extend his or her leg when sensor 216 indicates a predetermined orientation of the patient's leg. Because the sensed ECAP signals are associated with a much lower latency than the received sensor data (as described above), processing circuitry 214 may further use characteristics of the sensed ECAP signals to more-precisely determine both when to initiate stimulation delivery, as well as when to terminate the stimulation delivery, to more-effectively enhance the patient bodily movement or function.

In some examples, sensor 216 may indicate patient activity, and processing circuitry 214 may increase the frequency of control pulses and ECAP sensing in response to detecting increased patient activity. In one example, processing circuitry 214 may initiate control pulses and corresponding ECAP sensing in response to a signal from sensor 216 indicating that patient activity has exceeded an activity threshold. Conversely, processing circuitry 214 may decrease the frequency of control pulses and ECAP sensing in response to detecting decreased patient activity. For example, in response to sensor 216 no longer indicating that the sensed patient activity exceeds a threshold, processing circuitry 214 may suspend or stop delivery of control pulses and ECAP sensing. In this manner, processing circuitry 214 may dynamically deliver control pulses and sense ECAP signals based on patient activity to reduce power consumption of the system when the electrode-to-neuron distance is not likely to change and increase system response to ECAP changes when electrode-to-neuron distance is likely to change. IMD 200 may include additional sensors within the housing of IMD 200 and/or coupled via one of leads 130 or other leads. In addition, IMD 200 may receive sensor signals wirelessly from remote sensors via telemetry module 213, for example. In some examples, one or more of these remote sensors may be external to patient 105 (e.g., carried on the external surface of the skin, attached to clothing, or otherwise positioned external to the patient 105). In some examples, signals from sensor 216 may indicate a position or body state (e.g., sleeping, awake, sitting, standing, or the like) of patient 105, and processing circuitry 214 may select target ECAP characteristic values according to the indicated position or body state.

Telemetry module 213 supports wireless communication between IMD 200 and an external programmer 300 (FIG. 2B) or another computing device under the control of processing circuitry 214. Processing circuitry 214 of IMD 200 may receive, as updates to programs, values for various stimulation parameters such as amplitude and electrode combination, from the external programmer via telemetry module 213. Updates to the therapy stimulation programs 217 and ECAP test stimulation programs 218 may be stored within memory 215. Telemetry module 213 in IMD 200, as well as telemetry circuits in other devices and systems described herein, such as the external programmer, may accomplish communication by radiofrequency (RF) communication techniques. In addition, telemetry module 213 may communicate with an external medical device programmer (not shown in FIG. 2A) via proximal inductive interaction of IMD 200 with the external programmer. The external programmer may be one example of external programmer 150 of FIG. 1. Accordingly, telemetry module 213 may send information to the external programmer on a continuous basis, at periodic intervals, or upon request from IMD 110 or the external programmer.

Power source 219 delivers operating power to various components of IMD 200. Power source 219 may include a rechargeable or non-rechargeable battery and a power-generation circuit to produce the operating power. Recharging may be accomplished through proximal inductive interaction between an external charger and an inductive charging coil within IMD 200. In other examples, traditional primary cell batteries may be used.

According to the techniques of the disclosure, stimulation generator 211 of IMD 200 receives, via telemetry module 213, instructions to deliver SCS therapy according to therapy stimulation programs 217 to at least one target tissue site located on the spinal cord on a caudal side of a spinal cord injury relative to a patient's brain), via a plurality of electrode combinations of electrodes 232, 234 of leads 230 and/or a housing of IMD 200. Stimulation generator 211 may receive, via telemetry module 213, user instructions to deliver control stimulation to the patient according to ECAP test stimulation programs 218. Each pulse of a plurality of control pulses may elicit an ECAP that is sensed by sensing circuitry 212 via some of electrodes 232 and 234. ECAP test stimulation programs 218 may instruct stimulation generator 211 to deliver a plurality of control pulses interleaved with at least some of the plurality of informed pulses. Processing circuitry 214 may receive, via an electrical signal sensed by sensing circuitry 212, information indicative of an ECAP signal (e.g., a numerical value indicating a characteristic of the ECAP in electrical units such as voltage or power) produced in response to the control stimulation. Therapy stimulation programs 217 may be updated according to the ECAPs recorded at sensing circuitry 212 according to the following techniques.

In one example, the plurality of informed pulses each have a pulse width of greater than approximately 300 μs and less than approximately 2000 μs (i.e., 2 milliseconds). In some examples, the informed pulse width is greater than approximately 300 μs and less than approximately 800 μs. In another example, the informed pulse width is greater than approximately 300 μs and less than approximately 500 μs. In one example, informed pulses have a pulse width of approximately 450 μs and a pulse frequency of approximately 60 Hertz. Amplitude (current and/or voltage) for the informed pulses may be between approximately 0.5 mA (or volts) and approximately 10 mA (or volts), although amplitude may be lower or greater in other examples. In some examples, the pulse width of the informed pulses may be less than 300 μs. In some examples, the system may deliver informed pulses from two or more stimulation programs such that the informed pulses from one stimulation program have at least one different parameter value than the informed pulses from another stimulation program. As described above, the plurality of informed pulses may include multiple consecutive, discrete informed pulses delivered between a pair of discrete control pulses. In this manner, the system may be configured to deliver a train of control pulses, where one, two, three, four, or more informed pulses are delivered between consecutive control pulses of the train of control pulses. Each of the informed pulses may define a pulse width that is shorter or longer than a pulse width of the control pulses.

Each control pulse of the plurality of control pulses may have a pulse width of less than approximately 300 μs. In one example, each control pulse of the plurality of control pulses may be a bi-phasic pulse with a positive phase having a width of approximately 100 μs, a negative phase having a width of approximately 100 μs, and an interphase interval having a width of approximately 30 μs. In some examples, the positive phase and negative phase may each be 90 μs or 120 μs in other examples. In other examples, the control pulses may each have a pulse width of approximately 60 μs or smaller. Due to the relatively long pulse widths of the plurality of informed pulses, sensing circuitry 212 may be incapable of adequately recording an ECAP signals elicited from an informed pulse because the informed pulse itself will occur during the ECAP signal and obscure the ECAP signal. However, stimulation pulses with pulse widths less than approximately 300 microseconds, such as the plurality of control pulses, may be suited to elicit an ECAP which can be sensed after the control pulse is completed at sensing circuitry 212 via two or more of electrodes 232 and 234. In some examples, the control pulses may be non-therapeutic pulses in that the control pulses do not contribute to therapy for the patient. In other examples, the control pulses may fully provide or partially contribute to the therapy received by the patient by reducing or eliminating symptoms and/or a condition of the patient.

Control pulses delivered for the purpose of eliciting detectable ECAP signals may have a current amplitude between approximately 1 mA and 12 mA in some examples, but higher or lower amplitudes may be used in other examples. The frequency of the control pulses may be between approximately 50 Hertz and 400 Hertz in some examples, which may match the predetermined pulse frequency of the informed pulses when one control pulse is delivered for each therapeutic pulse. The predetermined pulse frequency may be a single frequency or a varied frequency over time (e.g., the interpulse interval may change over time according to predetermined pattern, formula, or schedule). In some examples, the system may change the predetermined pulse frequency based on patient input or a sensed parameter such as patient posture or activity. Such a relationship may be present when the control pulses are fully interleaved (e.g., alternating) with the informed pulses. However, the frequency of the control pulses may be delivered at a higher frequency than then informed pulses when two or more control pulses are delivered between consecutive informed pulses. In other examples, the frequency of the control pulses may be delivered at a lower frequency than the informed pulses when at least some informed pulses are delivered without a control pulse delivered between them. The frequency of the control pulses may be delivered at a frequency that varies over time if the system is configured to adjust control pulse delivery, and the resulting ECAP sensing, based on other factors such as patient activity.

In one example, the predetermined pulse frequency of the plurality of informed pulses may be less than approximately 400 Hertz. In some examples, the predetermined pulse frequency of the plurality of informed pulses may be between approximately 50 Hertz and 70 Hertz. In one example, the predetermined pulse frequency of the plurality of informed pulses may be approximately 60 Hertz. However, the informed pulses may have frequencies greater than 400 Hertz or less than 50 Hertz in other examples. In some examples, the predetermined pulse frequency of the informed pulses may be a single frequency or a frequency that varies over time. In addition, the informed pulses may be delivered in bursts of pulses, with interburst frequencies of the pulses being low enough such that a control pulse and sensed ECAP can still fit within the window between consecutive informed pulses delivered within the burst of informed pulses.

Since each informed pulse of the plurality of informed pulses may be sensed as an artifact that covers, or obscures, the sensing of at least one ECAP, the plurality of control pulses may be delivered to the patient during a plurality of time events. For example, a time event (e.g., a window) of the plurality of time events may be a time (e.g., a window) between consecutive informed pulses of the plurality of informed pulses at the predetermined pulse frequency. One or more control pulses of the plurality of control pulses may be delivered to the patient during each time event. Consequently, the control pulses may be interleaved with at least some of the informed pulses such that the plurality of control pulses are delivered to the patient while informed pulses are not delivered. In one example, an ECAP elicited from to a control pulse delivered during a time event may be recorded by sensing module 212 during the same time event. In another example, two or more ECAPs responsive to two or more respective control pulses delivered during a time event may be recorded by sensing module 212 during the same time event.

In some examples, therapy stimulation programs 217 may be updated according to a plurality of ECAPs received in response to the plurality of control pulses delivered to the patient according to ECAP test stimulation programs 218. For instance, processing circuitry 214 may update therapy stimulation programs 217 in real time by comparing one or more characteristics of ECAPs sensed by sensing module 212 with target ECAP characteristics stored in memory 215 (e.g., patient ECAP characteristics 222). For example, processing circuitry 214 is configured to determine the amplitude of each ECAP signal received at sensing module 212, and processing circuitry 214 is further configured to determine the representative amplitude of at least one respective ECAP signal and compare the representative amplitude of a series of ECAP signals to a target ECAP adjustment window (e.g., the target ECAP amplitude plus and minus a variance which is stored in patient ECAP characteristics 222). The target ECAP adjustment window may thus be a range of amplitudes deviating from target ECAP amplitude. For instance, the target ECAP adjustment window may span from a lower-bound amplitude value (e.g., the target ECAP amplitude minus the variance) to an upper-bound amplitude value (e.g., the target ECAP amplitude plus the variance). Generally, the lower-bound amplitude value is less than the target ECAP amplitude, and the upper-bound amplitude value is greater than target ECAP amplitude.

If the representative amplitude of the at least one respective ECAP signal (e.g., an amplitude of a single ECAP signal or an average of two or more ECAP amplitudes) is greater than the upper-bound amplitude value, processing circuitry 214 may adjust one or more of therapy stimulation programs 217 and ECAP test stimulation programs 218 to decrease the amplitude of informed pulses and control pulses following the at least one respective ECAP. The amplitude of informed pulses and control pulses may be decreased by different predetermined steps or different predetermined percentages. Additionally, if the representative amplitude of the at least one respective ECAP is less than the lower-bound amplitude value, processing circuitry 214 may adjust therapy stimulation programs 217 and ECAP test stimulation programs 218, and the programs 217 and 218 may instruct stimulation generator 211 to increase the amplitude of informed pulses and control pulses following the at least one respective ECAP. Moreover, if the representative amplitude of the at least one respective ECAP is greater than the lower-bound amplitude value and less than the upper-bound amplitude value, processing circuitry 214 may not change programs 217 and 218, and stimulation generator 211 may maintain the amplitude of the informed pulses following the at least one respective ECAP. In one example, adjusting the programs 217 and 218 may include changing one or more parameters of the plurality of informed pulses and the plurality of control pulses. In one example, the at least one respective ECAP may include a series of four consecutive ECAPs.

Processing circuitry 214, in one example, may change the amplitude of the informed pulses and the control pulses following the at least one respective ECAP inversely proportional to the difference between target ECAP amplitude and the representative amplitude of the at least one respective ECAP. For instance, if the representative amplitude of the at least one respective ECAP is 20% lower than the target ECAP amplitude, then processing circuitry 214 may update therapy programs 217 and 218 such that the amplitude of informed pulses and the control pulses is increased by 20%. In one example, the representative amplitude may be the mean amplitude of two or more respective ECAP signals sensed by sensing module 212. In other examples, the representative amplitude may be the median amplitude of two or more respective ECAP signals, or a rolling average of two or more respective ECAP signals.

In another example, processing circuitry 214 may determine the amplitude of a respective ECAP signal sensed by sensing module 212. In response to a comparison between the amplitude of the respective ECAP signal and the target ECAP amplitude stored in patient ECAP characteristics 222, processing circuitry 214 may determine a percentage difference between the amplitude of the respective ECAP signal and target ECAP amplitude. Consequently, processing circuitry 214 may adjust the amplitude of subsequent informed pulses to be inversely proportional to the percentage difference between the amplitude of the respective ECAP and target ECAP amplitude.

In other examples, processing circuitry 214 may use the representative amplitude of the at least one respective ECAP to change other parameters of informed pulses to be delivered, such as pulse width, pulse frequency, and pulse shape. All of these parameters may contribute to the intensity of the informed pulses, and changing one or more of these parameter values may effectively adjust the informed pulse intensity to compensate for the changed distance between stimulation electrodes and the nerves indicated by the representative amplitude of the ECAP signals.

In some examples in which leads 230 include linear 8-electrode leads (not pictured in FIG. 2A), sensing and stimulation delivery may each be performed using a different set of electrodes. For instance, in a linear 8-electrode lead, each electrode may be numbered consecutively from 0 through 7. A control pulse may be generated using electrode 1 as a cathode and electrodes 0 and 2 as anodes (e.g., a guarded cathode), and a respective ECAP signal may be sensed using electrodes 6 and 7, located on the opposite end of the electrode array. This strategy may minimize the interference of the stimulation pulse with the sensing of the respective ECAP. Other electrode combinations may be implemented, and the electrode combinations may be changed using the patient programmer via telemetry module 213. For example, stimulation electrodes and sensing electrodes may be positioned closer together. Shorter pulse widths for the control pulses may allow the sensing electrodes to be closer to the stimulation electrodes.

ECAP feedback rules 221 may define how processing circuitry 214 uses the sensed ECAP signals as feedback for changing one or more parameters that define informed pulses and stored as therapy stimulation programs 217. For example, ECAP feedback rules 221 may specify that the percentage difference between the representative ECAP amplitude and the target ECAP amplitude is used to inversely adjust the current amplitude of informed pulses to the same proportion as the percentage difference. As another example, ECAP feedback rules 221 may specify that the difference between the target ECAP amplitude is multiplied by a gain value and added to the previous current amplitude of the informed pulses and control pulses. In any case, ECAP feedback rules 221 may instruct processing circuitry 14 how to adjust informed pulses and/or control pulses based on the sensed ECAP signals. In other examples, ECAP feedback rules 221 may instruct processing circuitry 214 to adjust an amplitude of stimulation pulses, or start or stop deliver of stimulation, in response to detecting the presence or absence of ECAP signals (e.g., an ECAP characteristic value above or below a minimum threshold or perception threshold).

In one example, sensor 216 may detect a change in activity or a change in posture of patient 105 (FIG. 1). Processing circuitry 214 may receive an indication from sensor 216 that the activity level or posture of patient 105 has changed, and processing circuitry 214 may be configured to initiate or change the delivery of the plurality of control pulses according to the ECAP test stimulation programs 218. For example, processing circuitry 214 may increase the frequency of control pulse delivery and respective ECAP sensing in response to receiving an indication that the patient activity has increased, which may indicate that the distance between electrodes 232, 234 and nerves will likely change. Alternatively, processing circuitry 214 may decrease the frequency of control pulse delivery and respective ECAP sensing in response to receiving an indication that the patient activity has decreased. In some examples, one or more parameters (e.g., frequency, amplitude, slew rate, pulse duration, or the like) may be adjusted (e.g., increased or decreased) in response to receiving an indication that the patient activity has changed. Processing circuitry 214 may be further configured to update therapy stimulation programs 217 and ECAP test stimulation programs 218 according to the signal received from sensor 216.

Figure 2B:
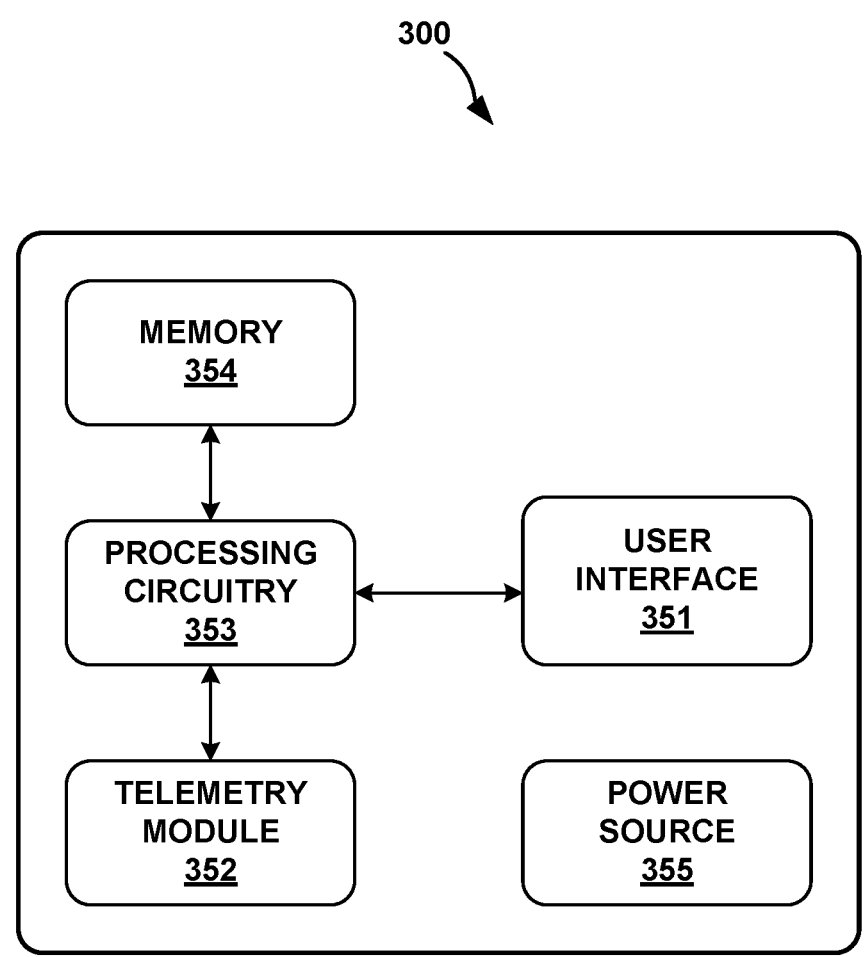
FIG. 2B is a block diagram of some example components of the external programmer of FIG. 1.

FIG. 2B is a block diagram illustrating some example components of an external programmer 300, which is an example of external programmer 150 of FIG. 1. Although programmer 300 may generally be described as a "handheld" device, programmer 300 may be a larger portable device or a more stationary device. In addition, in other examples, programmer 300 may be included as part of an external charging device or include the functionality of an external charging device. As illustrated in FIG. 2B, programmer 300 may include processing circuitry 353, a memory 354, a user interface 351, telemetry module 352, and a power source 355. Memory 354 may store instructions that, when executed by processing circuitry 353, cause processing circuitry 353 and external programmer 300 to provide the functionality ascribed to external programmers 150, 300 throughout this disclosure. Each of these components, circuitry, or modules, may include electrical circuitry that is configured to perform some, or all of the functionality described herein. For example, processing circuitry 353 may include processing circuitry configured to perform the processes discussed with respect to processing circuitry 353.

In general, programmer 300 comprises any suitable arrangement of hardware, alone or in combination with software and/or firmware, to perform the techniques attributed to programmer 300, and processing circuitry 353, user interface 351, and telemetry circuitry 352 of programmer 300. In various examples, programmer 300 may include one or more processors, such as one or more microprocessors, DSPs, ASICs, FPGAs, or any other equivalent integrated or discrete logic circuitry, as well as any combinations of such components. Programmer 300 also, in various examples, may include a memory 354, such as RAM, ROM, PROM, EPROM, EEPROM, flash memory, a hard disk, a CD-ROM, comprising executable instructions for causing the one or more processors to perform the actions attributed to them. Moreover, although processing circuitry 353 and telemetry circuitry 352 are described as separate modules, in some examples, processing circuitry 353 and telemetry circuitry 352 are functionally integrated. In some examples, processing circuitry 353 and telemetry circuitry 352 correspond to individual hardware units, such as ASICs, DSPs, FPGAs, or other hardware units.

Memory 354 (e.g., a storage device) may store instructions that, when executed by processing circuitry 353, cause processing circuitry 353 and programmer 300 to provide the functionality ascribed to programmers 150, 300 throughout this disclosure. For example, memory 354 may include instructions that cause processing circuitry 353 to obtain a parameter set from memory, select a spatial electrode movement pattern, or receive a user input and send a corresponding command to IMD 300, or instructions for any other functionality. In addition, memory 354 may include a plurality of programs, where each program includes a parameter set that defines therapy stimulation or control stimulation. Memory 354 may also store data received from a medical device (e.g., IMD 110). For example, memory 354 may store ECAP related data recorded at a sensing module of the medical device, and memory 354 may also store data from one or more sensors of the medical device.

User interface 351 may include a button or keypad, lights, a speaker for voice commands, a display, such as a liquid crystal (LCD), light-emitting diode (LED), or organic light-emitting diode (OLED). In some examples the display may be a touch screen. User interface 351 may be configured to display any information related to the delivery of electrical stimulation, identified patient behaviors, sensed patient parameter values, patient behavior criteria, or any other such information. User interface 351 may also receive user input via user interface 351. The input may be submitted by a user, for example, by pressing a button on a keypad or by selecting an icon from a touch screen. The input may request, as non-limiting examples, the starting or stopping of SCS therapy delivery, a new spatial electrode movement pattern or a change to an existing spatial electrode movement pattern, or some other change to the delivery of electrical stimulation.

Telemetry module 352 may support wireless communication between the medical device 110 of FIG. 1 and programmer 300 under the control of processing circuitry 353. Telemetry module 352 may also be configured to communicate with another computing device via wireless communication techniques, or direct communication through a wired connection. In some examples, telemetry module 352 provides wireless communication via an RF or proximal inductive medium. In some examples, telemetry module 352 includes an antenna, which may take on a variety of forms, such as an internal and/or external antenna.

Examples of local wireless communication techniques that may be employed to facilitate communication between programmer 300 and IMD 110 of FIG. 1 include RF communication according to the 802.11 or Bluetooth specification sets or other standard or proprietary telemetry protocols. In this manner, other external devices may be capable of communicating with programmer 300 without needing to establish a secure wireless connection. As described herein, telemetry circuitry 352 may be configured to transmit a spatial electrode movement pattern or other stimulation parameter values to IMD 110 for delivery of electrical stimulation therapy.

In some examples, selection of parameters or therapy stimulation programs may be transmitted to medical device 110 for delivery to patient 105. In other examples, the therapy may include medication, activities, or other instructions that patient 105 must perform themselves or that a caregiver must perform for patient 105. In some examples, programmer 300 may provide visual, audible, and/or tactile notifications indicating that there are new instructions. Programmer 300 may require the receipt of user input acknowledging that the instructions have been completed, in some examples.

According to techniques of the disclosure, user interface 351 of external programmer 300 receives an indication, e.g., from a clinician, instructing a processor 214 of medical device 200 (FIG. 2A) to update one or more therapy stimulation programs 217 or to update one or more ECAP test stimulation programs 218. Updating therapy stimulation programs 217 and ECAP test stimulation programs 218 may include changing one or more parameters of the stimulation pulses delivered by medical device 200 according to the programs, such as amplitude, pulse width, frequency, pulse shape, or other parameters of the informed pulses and/or control pulses. User interface 351 may also receive instructions from the clinician commanding any electrical stimulation, including therapy stimulation and control stimulation to commence or to cease.

The architecture of programmer 300 illustrated in FIG. 2B is shown as an example. The techniques as set forth in this disclosure may be implemented in the example programmer 300 of FIG. 2B, as well as in other types of systems not described specifically herein. Nothing in this disclosure should be construed so as to limit the techniques of this disclosure to the example architecture illustrated by FIG. 2B.

Figure 3:
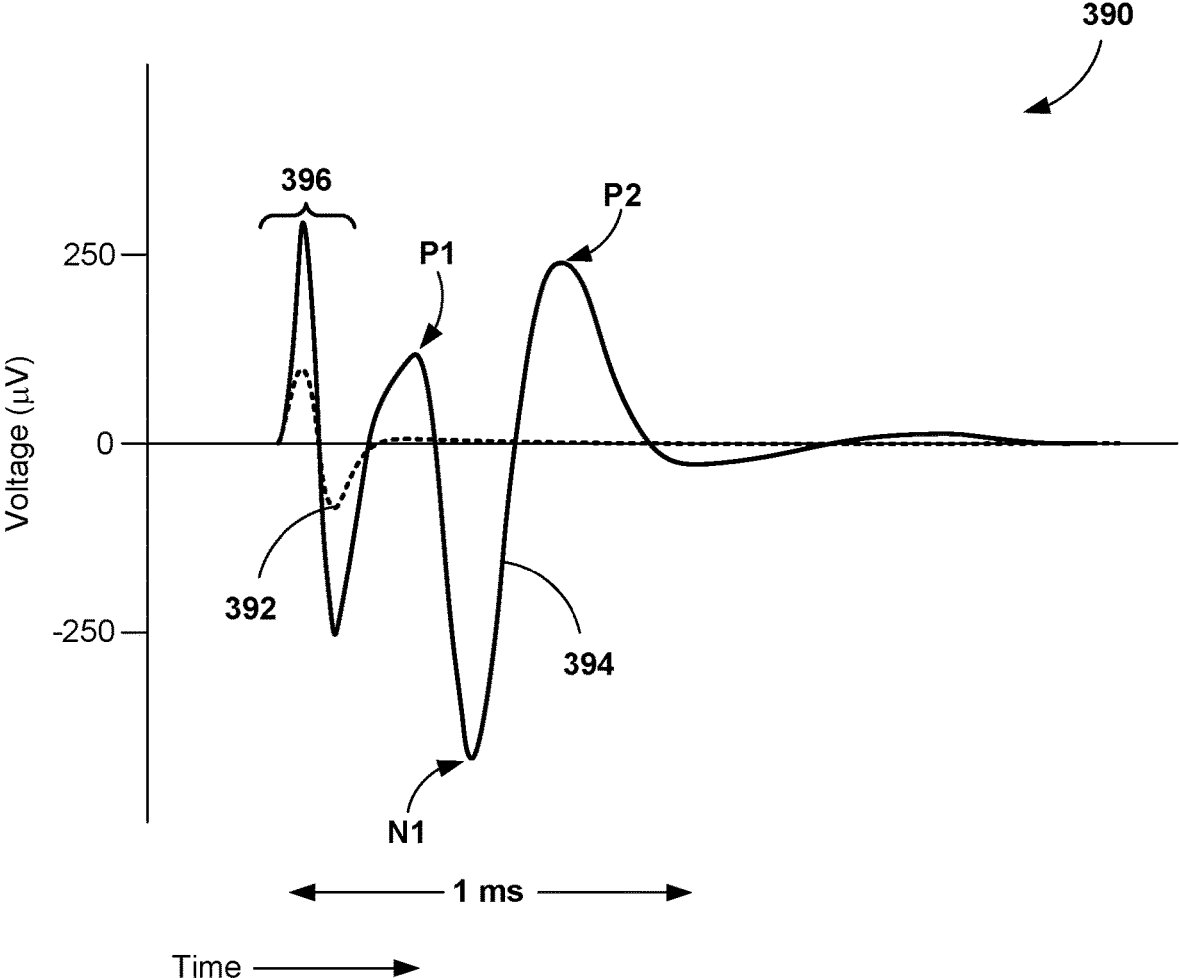
FIG. 3 is a graph of an example of evoked compound action potentials (ECAPs) sensed for respective stimulation pulses.

FIG. 3 is a graph 390 of an example of evoked compound action potentials (ECAPs) sensed for respective stimulation pulses. As shown in FIG. 3, graph 390 shows example ECAP signal 392 (dotted line) and ECAP signal 394 (solid line). Each of ECAP signals 392 and 394 may be sensed from control pulses that were delivered from a guarded cathode and bi-phasic pulses including an interphase interval between each positive and negative phase of the pulse. The guarded cathode of the stimulation electrodes may be located at one end of an 8-electrode lead, while two sensing electrodes are provided at the opposite end of the 8-electrode lead. ECAP signal 392 illustrates the sensed voltage amplitude resulting from a sub-threshold stimulation pulse. Peaks 396 of ECAP signal 392 are detected and represent the artifact of the delivered control pulse. However, no propagating signal is detected after the artifact in ECAP signal 392 because the control pulse was sub-threshold.

In contrast to ECAP signal 392, ECAP signal 394 represents the sensed voltage amplitude resulting from a supra-threshold control pulse. Peak(s) 396 of ECAP signal 394 are detected and represent the artifact of the delivered control pulse. After peak(s) 396, ECAP signal 394 also includes peaks P1, N1, and P2, which are three typical peaks representative of propagating action potentials from an ECAP. The example duration of the artifact and peaks P1, N1, and P2 is approximately 1 millisecond (ms). When detecting the ECAP of ECAP signal 394, different characteristics may be identified. For example, the characteristic of the ECAP may be the amplitude between N1 and P2. This N1-P2 amplitude may be easily detectable even if the artifact impinges on P1, a relatively large signal, and the N1-P2 amplitude may be minimally affected by electronic drift in the signal. In other examples, the characteristic of the ECAP used to control informed pulses may be an amplitude of P1, N1, or P2 with respect to a neutral (e.g., zero) voltage. In some examples, the characteristic of the ECAP used to control informed pulses may be a sum of two or more of peaks P1, N1, or P2. In other examples, the characteristic of ECAP signal 394 may be the area under one or more of peaks P1, N1, and/or P2. In other examples, the characteristic of the ECAP may be a ratio of one of peaks P1, N1, or P2 to another one of the peaks. In some examples, the characteristic of the ECAP may be a slope between two points in the ECAP signal, such as the slope between N1 and P2. In other examples, the characteristic of the ECAP may be the time between two points of the ECAP, such as the time between N1 and P2. The time between two points in the ECAP signal may be referred to as a "latency" of the ECAP and may indicate the types of fibers being captured by the control pulse. ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Other characteristics of the ECAP signal may be used in other examples.

The amplitude of the ECAP signal increases with increased amplitude of the control pulse, as long as the pulse amplitude is greater than threshold such that nerves depolarize and propagate the signal. The target ECAP characteristic (e.g., the target ECAP amplitude) may be determined from the ECAP signal detected from a control pulse when informed pulses are determined to deliver effective therapy to the patient. The ECAP signal thus is representative of the distance between the stimulation electrodes and the nerves appropriate for the stimulation parameter values of the informed pulses delivered at that time. Therefore, IMD 110 may attempt to use detected changes to the measured ECAP characteristic value to change informed pulse parameter values and maintain the target ECAP characteristic value during informed pulse delivery.

Figure 4A:
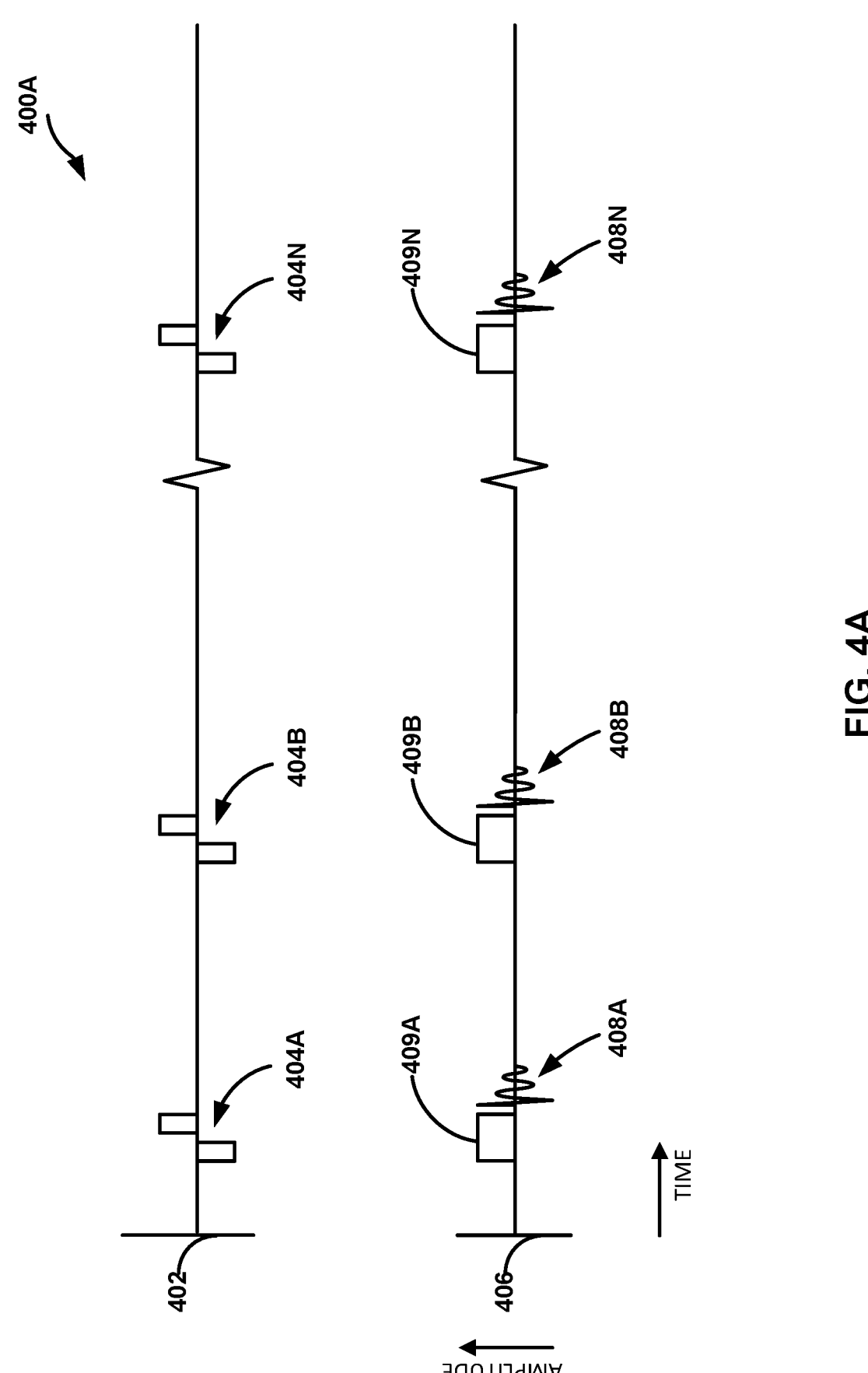
FIG. 4A is a timing diagram illustrating an example of electrical stimulation pulses and respective sensed ECAPs.

FIG. 4A is a timing diagram 400A illustrating an example of electrical stimulation pulses and respective sensed ECAP signals, in accordance with one or more techniques of this disclosure. For example, FIG. 4A is described with reference to IMD 200 of FIG. 2. As illustrated, timing diagram 400A includes first channel 402, a plurality of control pulses 404A-404N (collectively "control pulses 404"), second channel 406, a plurality of respective ECAPs 408A-408N (collectively "ECAPs 408"), and a plurality of stimulation interference signals 409A-409N (collectively "stimulation interference signals 409"). In the example of FIG. 4A, control pulses 404 may also provide therapy to the patient, such as initiating nerve function lost due to the spinal cord injury, and informed pulses are not necessary for therapy.

First channel 402 is a time/voltage (and/or current) graph indicating the voltage (or current) of at least one electrode of electrodes 232, 234. In one example, the stimulation electrodes of first channel 402 may be located on the opposite side of the lead as the sensing electrodes of second channel 406. Control pulses 404 may be electrical pulses delivered to the spinal cord of the patient by at least one of electrodes 232, 234, and control pulses 404 may be balanced biphasic square pulses with an interphase interval. In other words, each of control pulses 404 are shown with a negative phase and a positive phase separated by an interphase interval. For example, a control pulse 404 may have a negative voltage for the same amount of time and amplitude that it has a positive voltage. It is noted that the negative voltage phase may be before or after the positive voltage phase. Control pulses 404 may be delivered according to ECAP test stimulation programs 218 stored in storage device 212 of IMD 200, and ECAP test stimulation programs 218 may be updated according to user input via an external programmer and/or may be updated according to a signal from sensor(s) 222. In one example, control pulses 404 may have a pulse width of less than approximately 300 microseconds (e.g., the total time of the positive phase, the negative phase, and the interphase interval is less than 300 microseconds). In another example, control pulses 404 may have a pulse width of approximately 100 µs for each phase of the bi-phasic pulse. However, control pulses 404 may have longer pulses widths in other examples. As illustrated in FIG. 4A, control pulses 404 may be delivered via one or more electrodes that deliver or sense signals corresponding to channel 402. Delivery of control pulses 404 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode. For some patients, control pulses 404 may sufficiently provide therapy that treats the condition and/or symptoms of the patient. Therefore, additional informed pulses may not be needed for these patients or for at least some aspect of the therapy for these patients.

Second channel 406 is a time/voltage (and/or current) graph indicating the voltage (or current) of at least one electrode of electrodes 232, 234. In one example, the electrodes of second channel 406 may be located on the opposite side of the lead as the electrodes of first channel 402. ECAPs 408 may be sensed at electrodes 232, 234 from the spinal cord of the patient in response to control pulses 404. ECAPs 408 are electrical signals which may propagate along a nerve away from the origination of control pulses 404. In one example, ECAPs 408 are sensed by different electrodes than the electrodes used to deliver control pulses 404. As illustrated in FIG. 4A, ECAPs 408 may be recorded on second channel 406.

Stimulation interference signals 409A, 409B, and 409N (e.g., the artifact of the stimulation pulses) may be sensed by leads 230 and may be sensed during the same period of time as the delivery of control pulses 404. Since the interference signals may have a greater amplitude and intensity than ECAPs 408, any ECAPs arriving at IMD 200 during the occurrence of stimulation interference signals 409 may not be adequately sensed by sensing circuitry 206 of IMD 200. However, ECAPs 408 may be sufficiently sensed by sensing circuitry 206 because each ECAP 408 falls after the completion of each a control pulse 404. As illustrated in FIG. 4A, stimulation interference signals 409 and ECAPs 408 may be recorded on channel 406.

Figure 4B:
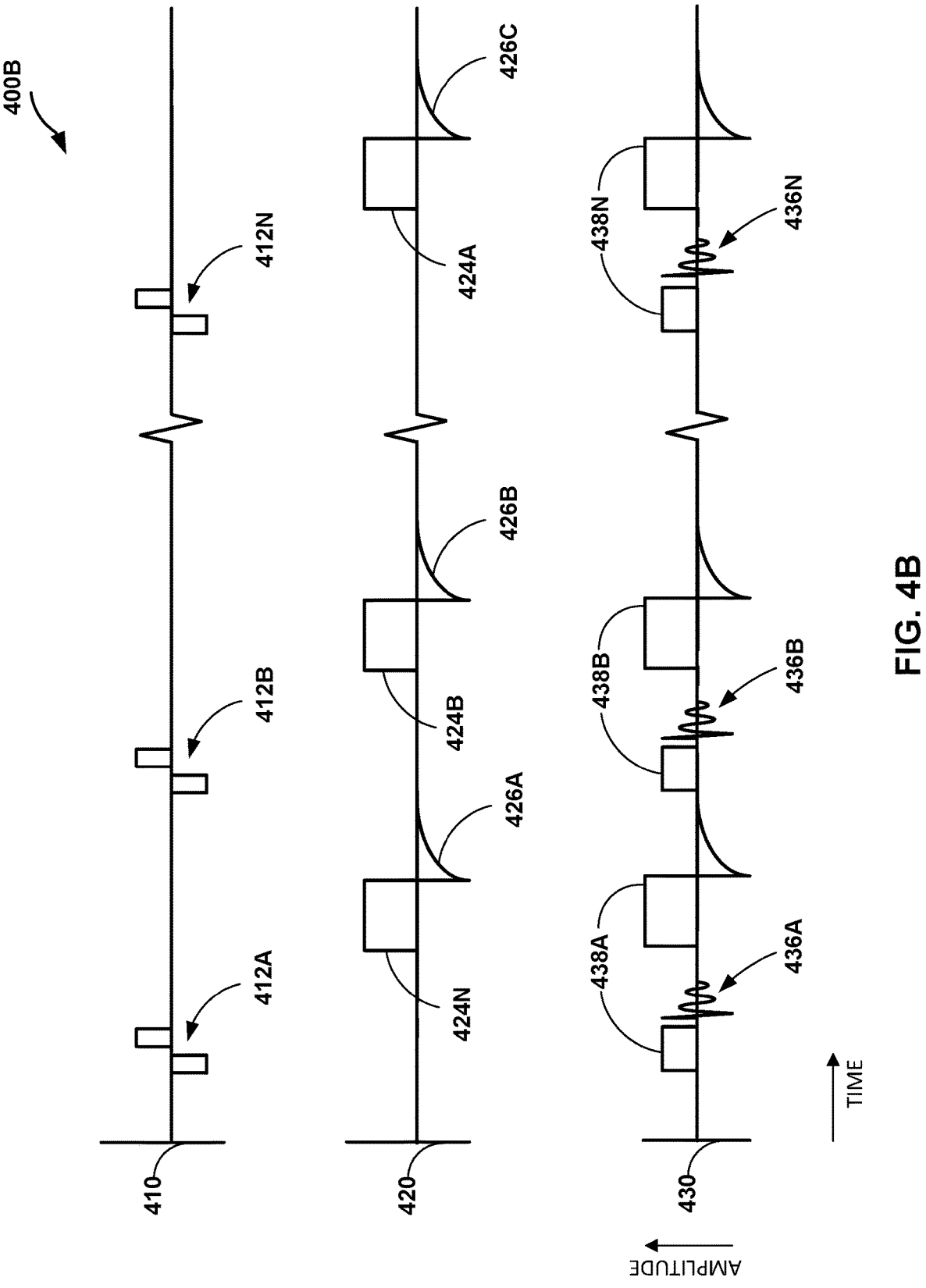
FIG. 4B is a timing diagram illustrating another example of electrical stimulation pulses and respective sensed ECAPs.

FIG. 4B is a timing diagram 400B illustrating one example of electrical stimulation pulses and respective sensed ECAPs according to some techniques of the disclosure. For convenience, FIG. 4B is described with reference to IMD 200 of FIG. 2A. As illustrated, timing diagram 400B includes first channel 410, a plurality of control pulses 412A-412N (collectively "control pulses 412"), second channel 420, a plurality of informed pulses 424A-424N (collectively "informed pulses 424") including passive recharge phases 426A-426N (collectively "passive recharge phases 426"), third channel 430, a plurality of respective ECAPs 436A-436N (collectively "ECAPs 436"), and a plurality of stimulation interference signals 438A-438N (collectively "stimulation interference signals 438").

First channel 410 is a time/voltage (and/or current) graph indicating the voltage (or current) of at least one electrode of electrodes 232, 234. In one example, the stimulation electrodes of first channel 410 may be located on the opposite side of the lead as the sensing electrodes of third channel 430. Control pulses 412 may be electrical pulses delivered to the spinal cord of the patient by at least one of electrodes 232, 234, and control pulses 412 may be balanced biphasic square pulses with an interphase interval. In other words, each of control pulses 412 are shown with a negative phase and a positive phase separated by an interphase interval. For example, a control pulse 412 may have a negative voltage for the same amount of time and amplitude that it has a positive voltage. It is noted that the negative voltage phase may be before or after the positive voltage phase. Control pulses 412 may be delivered according to ECAP test stimulation programs 218 stored in memory 250 of IMD 200, and ECAP test stimulation programs 218 may be updated according to user input via an external programmer and/or may be updated according to a signal from sensor 216. In one example, control pulses 412 may have a pulse width of less than approximately 300 microseconds (e.g., the total time of the positive phase, the negative phase, and the interphase interval is less than 300 microseconds). In another example, control pulses 412 may have a pulse width of approximately 100 μs for each phase of the bi-phasic pulse. As illustrated in FIG. 4B, control pulses 412 may be delivered via one or more electrodes that deliver or sense signals corresponding to channel 410. Delivery of control pulses 412 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 420 is a time/voltage (and/or current) graph indicating the voltage (or current) of at least one electrode of electrodes 232, 234 for the informed pulses. In one example, the electrodes of second channel 420 may partially or fully share common electrodes with the electrodes of first channel 410 and third channel 430. Informed pulses 424 may also be delivered by the same leads 230 that are configured to deliver control pulses 412. Informed pulses 424 may be interleaved with control pulses 412, such that the two types of pulses are not delivered during overlapping periods of time. However, informed pulses 424 may or may not be delivered by exactly the same electrodes that deliver control pulses 412. Informed pulses 424 may be monophasic pulses with pulse widths of greater than approximately 300 μs and less than approximately 1000 μs. In fact, informed pulses 424 may be configured to have longer pulse widths than control pulses 412. As illustrated in FIG. 4B, informed pulses 424 may be delivered on channel 420. As described above, in some examples (not shown in FIG. 4B), each informed pulse 424 may be replaced by a plurality (or a "burst") of consecutive informed pulses delivered between a pair of consecutive control pulses 412 (e.g., between control pulses 412A, 412B). In this manner, the control pulses 412 may be described as being partially interleaved with informed pulses 424.

Informed pulses 424 may be configured for passive recharge. For example, each informed pulse 424 may be followed by a passive recharge phase 426 to equalize charge on the stimulation electrodes. Unlike a pulse configured for active recharge, wherein remaining charge on the tissue following a stimulation pulse is instantly removed from the tissue by an opposite applied charge, passive recharge allows tissue to naturally discharge to some reference voltage (e.g., ground or a rail voltage) following the termination of the informed pulse. In some examples, the electrodes of the medical device may be grounded at the medical device body. In this case, following the termination of informed pulse 424, the charge on the tissue surrounding the electrodes may dissipate to the medical device, creating a rapid decay of the remaining charge at the tissue following the termination of the pulse. This rapid decay is illustrated in passive recharge phases 426. Passive recharge phase 426 may have a duration in addition to the pulse width of the preceding informed pulse 424. In other examples (not pictured in FIG. 4B), informed pulses 424 may be bi-phasic pulses having a positive and negative phase (and, in some examples, an interphase interval between each phase) which may be referred to as pulses including active recharge. An informed pulse that is a bi-phasic pulse may or may not have a following passive recharge phase. Informed pulses 424 may be defined, and be a part of, one or more stimulation programs. Although each of informed pulses 424 are illustrated as having the same parameter values (e.g., the same pulse width, amplitude, and pulse shape), some of informed pulses 424 may have one or more parameters that have different values from each other.

Third channel 430 is a time/voltage (and/or current) graph indicating the voltage (or current) of at least one electrode of electrodes 232, 234. In one example, the electrodes of third channel 430 may be located on the opposite side of the lead as the electrodes of first channel 410. ECAPs 436 may be sensed at electrodes 232, 234 from the spinal cord of the patient in response to control pulses 412. ECAPs 436 are electrical signals which may propagate along a nerve away from the origination of control pulses 412. In one example, ECAPs 436 are sensed by different electrodes than the electrodes used to deliver control pulses 412. As illustrated in FIG. 4B, ECAPs 436 may be recorded on third channel 430.

Stimulation interference signals 438A, 438B, and 438N (e.g., the artifact of the stimulation pulses) may be sensed by leads 230 and may be sensed during the same period of time as the delivery of control pulses 412 and informed pulses 424. Since the interference signals may have a greater amplitude and intensity than ECAPs 436, any ECAPs arriving at IMD 200 during the occurrence of stimulation interference signals 438 may not be adequately sensed by sensing circuitry 212 of IMD 200. However, ECAPs 436 may be sufficiently sensed by sensing circuitry 212 because each ECAP 436 falls after the completion of each a control pulse 412 and before the delivery of the next informed pulse 424. As illustrated in FIG. 4B, stimulation interference signals 438 and ECAPs 436 may be recorded on channel 430. In other examples, control pulses 412 and informed pulses 424 may have similar pulse widths, but vary in one or more other parameter values.

Figure 5:
FIG. 5 is a flowchart illustrating an example technique for adjusting the delivery of stimulation pulses of in response to an input.
Figure 5:
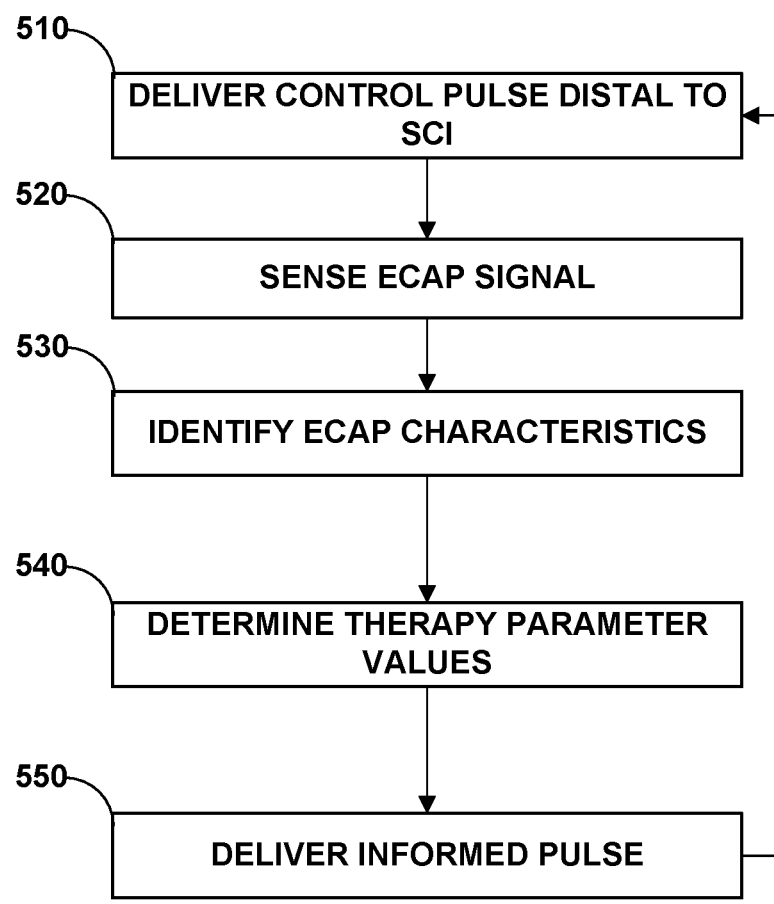

FIG. 5 is a flowchart illustrating an example closed-loop, ECAP-based stimulation-therapy operation 500. For convenience, FIG. 5 is described with respect to IMD 200 of FIG.

2A. However, the techniques of FIG. 5 may be performed by different components of IMD 200 or by additional or alternative medical devices.

In the example of FIG. 5, processing circuitry 214 controls delivery of one or more control stimulation pulses via an electrode combination of at least one lead 230 positioned at a target tissue site located caudally of a spinal cord injury of a patient (510). Processing circuitry 214 receives an ECAP signal, e.g., sensed by the same or a different electrode combination, elicited in response to the control stimulation pulses (520).

Processing circuitry 214 identifies one or more characteristics of the sensed ECAP signal (530). For instance, processing circuitry 214 may determine (e.g., measure) a signal width, amplitude, phase, slope, area-under-curve, delay, etc. Based on the identified ECAP characteristic(s), processing circuitry 214 determines a set of appropriate therapy parameter values that at least partially define subsequent control stimulation pulse(s) (540). For instance, identified ECAP characteristics (e.g., matching a characteristic pattern or signature characteristic 222 stored in memory 215) may indicate a volitional (e.g., locomotor or functional) intent of the patient, or an underlying neurophysiologic state of the patient, corresponding to a predetermined therapy program 217 stored in memory 215 that includes the defined set of therapy parameter values.

Processing circuitry 214 then controls delivery of informed stimulation pulse(s), via the electrode combination, for the treatment of at least one condition associated with the spinal cord injury of the patient, such as to enhance strength, locomotion, or bladder control; regulate blood pressure; induce a macro-function; or any other SCI-related condition amenable to stimulation therapy (550). Responsive to delivering the informed stimulation pulses, processing circuitry 214 may control delivery of subsequent control stimulation pulse(s), such that the control pulse(s) are interleaved with the informed stimulation pulse(s) (510).

Figure 6:
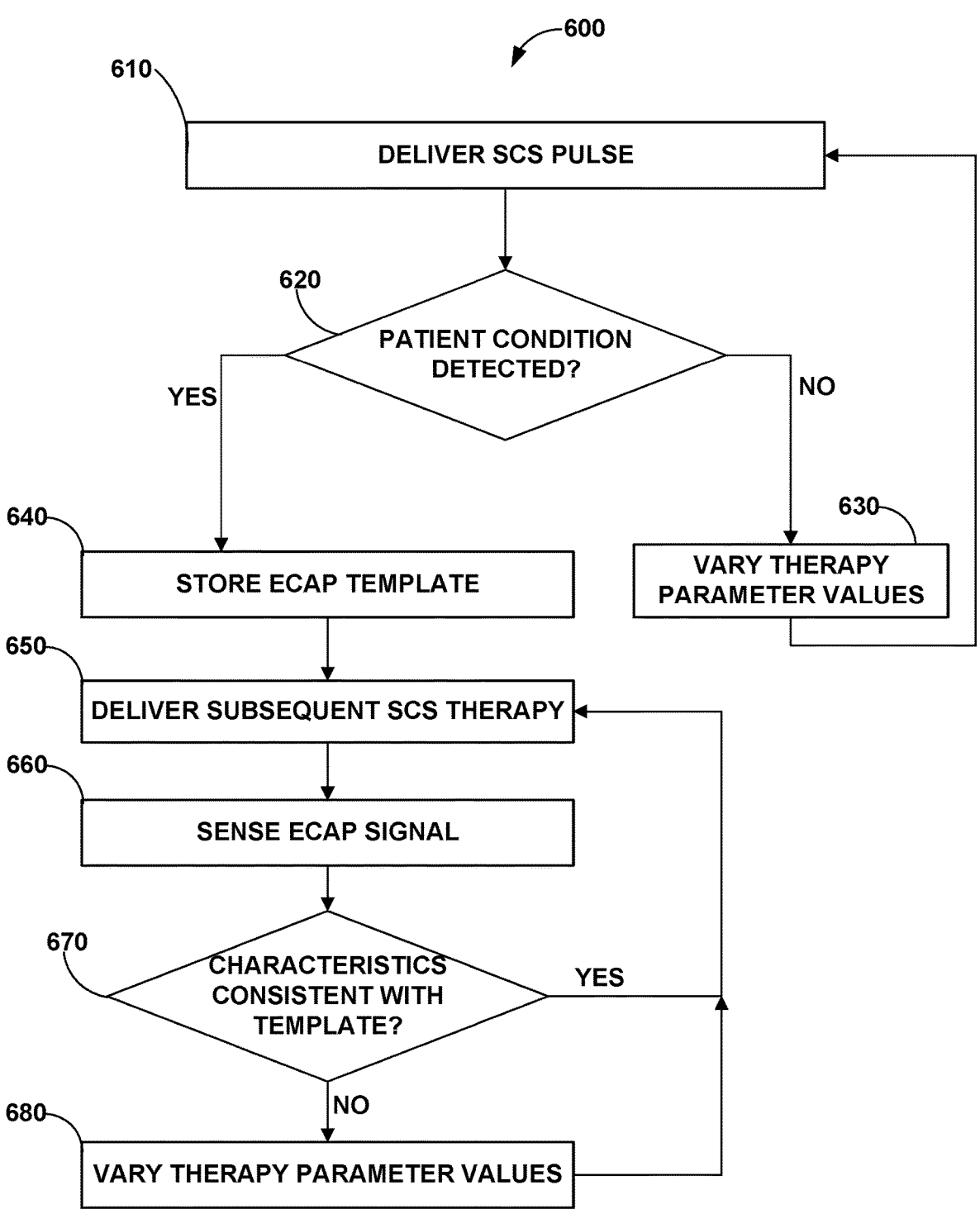
FIG. 6 is a flowchart illustrating an example operation for adjusting stimulation therapy.

FIG. 6 is a flowchart illustrating an example operation 600 for adjusting stimulation therapy. IMD 200 and processing circuitry 214 will be described in the example of FIG. 6, but other IMDs (such as IMD 110 of FIG. 1) or other devices or systems may perform, or partially perform, operation 600. Additionally, operation 600 as described below is performed with respect to one or more machine-learning algorithms of processing circuitry 214, however, in other examples, processing circuitry 214 may execute operation 600 using standard digital logic.

During an initial training phase, processing circuitry 214 controls the periodic delivery of spinal-cord-stimulation (SCS) pulses, such as epidural electrical spinal-cord-stimulation (EES) pulses, to at least one target tissue site located caudally of a spinal cord injury (SCI) of a patient (610). For instance, at least one lead 230, or electrodes carried thereon, coupled to IMD 200 may be positioned on a caudal side of the SCI from the patient's brain.

Processing circuitry 214 may prompt a user (e.g., provide an ongoing prompt for user input) to indicate whether a desired patient condition, associated with the spinal cord injury, was elicited in response to the delivered SCS (620). Examples of desirable patient conditions may include, as non-limiting examples, a patient bodily position, locomotion, bodily function, blood pressure, or the like. In some scenarios, the desired patient condition is not elicited in response to the delivered SCS ("NO" branch of 620). For instance, a user (e.g., the patient or a clinician) may submit user input indicating that the condition was not elicited, or a predetermined amount of time may expire without a user submitting user input, or an appropriate sensor may detect that the desired condition was not elicited. In such examples, processing circuitry 214 is configured to vary one or more of the therapy parameter values (e.g., pulse width, pulse amplitude, pulse frequency, pulse shape, etc.) (630) and deliver subsequent SCS pulse(s) according to the varied therapy parameter value(s) (610).

This cycle may continue until the desired patient condition is elicited ("YES" branch of 620). For instance, the user may submit user input indicating that the condition was elicited, or an appropriate sensor may detect that the desired condition was elicited. In response to receiving an indication of the elicited desired patient condition, processing circuitry captures and stores an ECAP "template" characterizing, e.g., a most-recent sensed ECAP signal elicited by the SCS (640). In examples in which processing circuitry is configured to execute one or more machine-learning algorithms, the algorithm(s) may now be considered to be "trained."

Processing circuitry 214 may continue to control delivery of subsequent SCS therapy (650) and sense respective ECAP signals (660). Periodically (e.g., after each stimulation pulse, or less frequently), processing circuitry 214 compares characteristics of the most-recent sensed ECAP signal to those of the stored template to determine whether the characteristics are consistent (e.g., are within threshold tolerances of the template values) (670). As long as the characteristics are consistent ("YES" branch of 670), processing circuitry 214 may continue to control the delivery of the SCS therapy with the existing parameter values (650). However, in instances in which identified ECAP characteristics are not consistent with the stored ECAP template ("NO" branch of 670), processing circuitry modifies one or more of the therapy parameter values (680) of the delivered SCS therapy (650) until values consistent with the stored ECAP template are regained.

The following examples are examples systems, devices, and methods described herein. Example 1: A method includes: delivering, via a first electrode combination, a first stimulation pulse to a portion of a spinal cord of a patient located caudally of a spinal cord injury location of the spinal cord of the patient; sensing, via a second electrode combination, an evoked compound action potential (ECAP) signal elicited by the first stimulation pulse; identifying, by processing circuitry, a characteristic of the ECAP signal; determining, by the processing circuitry and based on the characteristic of the ECAP signal, a therapy parameter value that at least partially defines a second stimulation pulse; and delivering the second stimulation pulse according to the determined therapy parameter value.

Example 2: The method of example 1, further including: storing data indicative of a plurality of ECAP signals sensed over a time period, the plurality of ECAP signals comprising the ECAP signal; and determining a trend from the data indicative of changes of the spinal cord of the patient over the time period.

Example 3: The method of any of examples 1 and 2, wherein determining at least the therapy parameter value for the second stimulation pulse includes determining at least the therapy parameter value that defines the stimulation pulse to contribute to induction of a macro-function of the patient.

Example 4: The method of example 3, further including iteratively determining therapy parameter values for respective subsequent stimulation pulses based on characteristics of respective ECAP signals to induce a body function associated with the macro-function of the patient.

Example 5: The method of any of examples 1 through 4, wherein the characteristic is a first characteristic and the ECAP signal is a first ECAP signal, and wherein the method further includes: determining a second characteristic of a second ECAP signal sensed via the electrode combination; and determining, based on the second characteristic of the second ECAP signal, to terminate delivery of subsequent stimulation pulses to induce a macro-function of the patient.

Example 6: The method of any of examples 1 through 5, wherein the ECAP signal includes a first ECAP signal, and wherein the method further includes: sensing, via a third electrode combination positioned cranially to the spinal cord injury location, a second ECAP signal; determining a characteristic of the third ECAP signal; and comparing the characteristic of the first ECAP signal sensed by the second electrode combination to the characteristic of the second ECAP signal sensed by the third electrode combination, wherein determining the therapy parameter value comprises determining, based on the comparison, the therapy parameter value.

Example 7: The method of any of examples 1 through 6, wherein determining the therapy parameter value includes determining the therapy parameter value to define one or more stimulation pulses comprising the second stimulation pulse to promote standing or locomotion of the patient.

Example 8: The method of any of examples 1 through 7, wherein determining the therapy parameter value includes determining the therapy parameter value to define one or more stimulation pulses comprising the second stimulation pulse to promote movement and strength in hands and upper limbs of the patient.

Example 9: The method of any of examples 1 through 8, wherein determining the therapy parameter value comprises determining the therapy parameter value to define one or more stimulation pulses comprising the second stimulation pulse to reduce a spasticity of the patient.

Example 10: The method of any of examples 1 through 9, wherein determining the therapy parameter value comprises determining the therapy parameter value to define one or more stimulation pulses comprising the second stimulation pulse to regulate a blood pressure or body temperature of the patient.

Example 11: The method of any of examples 1 through 10, wherein determining the therapy parameter value comprises determining the therapy parameter value to define one or more stimulation pulses comprising the second stimulation pulse to promote a sexual response or a bladder or bowel control of the patient.

Example 12: The method of any of examples 1 through 11, wherein determining the therapy parameter value comprises: determining, based on the characteristic of the ECAP signal, a volitional intent of the patient; and selecting, based on the determined volitional intent, a therapy program comprising the therapy parameter value.

Example 13: The method of any of examples 1 through 12, further comprising determining, based on the characteristic of the ECAP signal, a neurophysiologic state of the patient.

Example 14: The method of any of examples 1 through 13, wherein the characteristic of the ECAP signal comprises one of: a signal amplitude; a signal width; a signal latency; a signal slope; an area-under-the-curve (AUC) of the ECAP signal; a signal phasing; a signal curvature; an oscillatory pattern of the ECAP signal; a signal morphology; or a temporal stability of the ECAP signal.

Example 15: The method of any of examples 1 through 14, wherein sensing the ECAP signal comprises sampling a plurality of ECAP signals comprising the ECAP signal according to a predetermined sampling frequency.

Example 16: The method of example 15, wherein the predetermined sampling frequency comprises about 10 Hz to about 100 Hz.

Example 17: The method of any of examples 1 through 16, wherein the first stimulation pulse is a control stimulation pulse configured to elicit the ECAP signal, and wherein the second stimulation pulse is configured to contribute to stimulation therapy for the patient.

Example 18: The method of any of examples 1 through 17, wherein the characteristic of the ECAP signal indicates that the delivered stimulation is not appropriate due to stimulation of an incorrect anatomical position of the lead, and wherein determining the therapy parameter value comprises changing the second electrode combination for delivering the second stimulation pulse.

Example 19: The method of any of examples 1 through 18, wherein determining the therapy parameter value comprises applying a machine-learning model trained to identify the characteristic of the ECAP signal to produce the therapy parameter value, and wherein the therapy parameter value is configured to maintain a preferred ECAP signal characteristic.

Example 20: The method of example 19, wherein applying the machine-learning model comprises: varying therapy parameter values of the first stimulation pulse until a desired patient condition is elicited; sensing the ECAP signal at the time at which the desired patient condition is elicited; storing a template indicative of the sensed ECAP signal; and varying therapy parameter values of the second stimulation pulse to maintain sensed ECAP signals consisted with the stored template.

Example 21: The method of any of examples 1 through 20, further comprising receiving sensor data from one or more sensors disposed at a location separate from the spinal cord, wherein determining the therapy parameter value comprises determining the therapy parameter value based on the characteristic of the ECAP signal and based on the sensor data.

Example 22: The method of example 21, wherein the one or more sensors comprise at least one of an accelerometer, an EEG, or an EMG.

Example 23: The method of any of examples 1 through 22, wherein an implantable medical device comprises the processing circuitry.

Example 24: A system includes stimulation generation circuitry configured to: deliver, via a first electrode combination, a first stimulation pulse to a portion of a spinal cord of a patient located caudally of a spinal cord injury location of the spinal cord of the patient; and deliver a second stimulation pulse according to a determined therapy parameter value; and processing circuitry configured to: receive, via a second electrode combination, a sensed evoked compound action potential (ECAP) signal elicited by the first stimulation pulse; identify a characteristic of the ECAP signal; and determine, based on the characteristic of the ECAP signal, the therapy parameter value, wherein the therapy parameter value at least partially defines the second stimulation pulse.

Example 25: The system of example 24, wherein the processing circuitry is further configured to: store data indicative of a plurality of ECAP signals sensed over a time period, the plurality of ECAP signals comprising the ECAP signal; and determine a trend from the data indicative of changes of the spinal cord of the patient over the time period.

Example 26: The system of any of examples 24 and 25, wherein, to determine at least the therapy parameter value for the second stimulation pulse, the processing circuitry is configured to determine at least the therapy parameter value that defines the stimulation pulse to contribute to induction of a macro-function of the patient.

Example 27: The system of example 26, wherein the processing circuitry is further configured to iteratively determine therapy parameter values for respective subsequent stimulation pulses based on characteristics of respective ECAP signals to induce a body function associated with the macro-function of the patient.

Example 28: The system of any of examples 24 through 27, wherein, to determine the therapy parameter value, the processing circuitry is configured to determine the therapy parameter value to define one or more stimulation pulses comprising the second stimulation pulse to promote standing or locomotion of the patient.

Example 29: The system of any of examples 24 through 28, wherein, to determine the therapy parameter value, the processing circuitry is configured to determine the therapy parameter value to define one or more stimulation pulses comprising the second stimulation pulse to promote movement and strength in hands and upper limbs of the patient.

Example 30: The system of any of examples 24 through 29, wherein, to determine the therapy parameter value, the processing circuitry is configured to determine the therapy parameter value to define one or more stimulation pulses comprising the second stimulation pulse to reduce a spasticity of the patient.

Example 31: The system of any of examples 24 through 30, wherein, to determine the therapy parameter value, the processing circuitry is configured to determine the therapy parameter value to define one or more stimulation pulses comprising the second stimulation pulse to regulate a blood pressure or body temperature of the patient.

Example 32: The system of any of examples 24 through 31, wherein, to determine the therapy parameter value, the processing circuitry is configured to determine the therapy parameter value to define one or more stimulation pulses comprising the second stimulation pulse to promote a sexual response or a bladder or bowel control of the patient.

Example 33: The system of any of examples 24 through 32, wherein, to determine the therapy parameter value, the processing circuitry is configured to: determine, based on the characteristic of the ECAP signal, a volitional intent of the patient; and select, based on the determined volitional intent, a therapy program comprising the therapy parameter value.

Example 34: The system of any of examples 24 through 33, wherein, to determine the therapy parameter value, the processing circuitry is configured to apply a machine-learning model trained to identify the characteristic of the ECAP signal to produce the therapy parameter value, and wherein the therapy parameter value is configured to maintain a preferred ECAP signal characteristic.

Example 35: The system of example 34, wherein, to apply the machine-learning model, the processing circuitry is configured to: vary therapy parameter values of the first stimulation pulse until a desired patient condition is elicited; sense the ECAP signal at the time at which the desired patient condition is elicited; store a template indicative of the sensed ECAP signal; and vary therapy parameter values of the second stimulation pulse to maintain sensed ECAP signals consisted with the stored template.

Example 36: The system of any of examples 24 through 35, wherein the processing circuitry is further configured to receive sensor data from one or more sensors disposed at a location separate from the spinal cord, wherein, to determine the therapy parameter value, the processing circuitry is configured to determine the therapy parameter value based on the characteristic of the ECAP signal and based on the sensor data.

Example 37: The system of example 36, wherein the one or more sensors comprise at least one of an accelerometer, an EEG, or an EMG.

Example 38: A computer-readable storage medium includes control delivery, via a first electrode combination, a first stimulation pulse to a portion of a spinal cord of a patient located caudally of a spinal cord injury location of the spinal cord of the patient; sense an evoked compound action potential (ECAP) signal elicited by the first stimulation pulse; identify a characteristic of the ECAP signal; determine, based on the characteristic of the ECAP signal, a therapy parameter value that at least partially defines a second stimulation pulse; and control delivery of the second stimulation pulse according to the determined therapy parameter value.

Example 39: The storage medium of example 38, wherein the instructions further cause the processing circuitry to: store data indicative of a plurality of ECAP signals sensed over a time period, the plurality of ECAP signals comprising the ECAP signal; and determine a trend from the data indicative of changes of the spinal cord of the patient over the time period.

Example 40: The storage medium of any of examples 38 and 39, wherein, to determine at least the therapy parameter value for the second stimulation pulse, the instructions cause the processing circuitry to determine at least the therapy parameter value that defines the stimulation pulse to contribute to induction of a macro-function of the patient.

Example 41: The storage medium of example 40, wherein the instructions further cause the processing circuitry to iteratively determine therapy parameter values for respective subsequent stimulation pulses based on characteristics of respective ECAP signals to induce a body function associated with the macro-function of the patient.

Example 42: The storage medium of any of examples 38 through 41, wherein, to determine the therapy parameter value, the instructions cause the processing circuitry to determine the therapy parameter value to define one or more stimulation pulses comprising the second stimulation pulse to promote standing or locomotion of the patient.

Example 43: The storage medium of any of examples 38 through 42, wherein, to determine the therapy parameter value, the instructions cause the processing circuitry to determine the therapy parameter value to define one or more stimulation pulses comprising the second stimulation pulse to promote movement and strength in hands and upper limbs of the patient.

Example 44: The storage medium of any of examples 38 through 43, wherein, to determine the therapy parameter value, the instructions cause the processing circuitry to determine the therapy parameter value to define one or more stimulation pulses comprising the second stimulation pulse to reduce a spasticity of the patient.

Example 45: The storage medium of any of examples 38 through 44, wherein, to determine the therapy parameter value, the instructions cause the processing circuitry to determine the therapy parameter value to define one or more stimulation pulses comprising the second stimulation pulse to regulate a blood pressure or body temperature of the patient.

Example 46: The storage medium of any of examples 38 through 45, wherein, to determine the therapy parameter value, the instructions cause the processing circuitry to define one or more stimulation pulses comprising the second stimulation pulse to promote a sexual response or a bladder or bowel control of the patient.

Example 47: The storage medium of any of examples 38 through 46, wherein, to determine the therapy parameter value, the instructions cause the processing circuitry to: determine, based on the characteristic of the ECAP signal, a volitional intent of the patient; and select, based on the determined volitional intent, a therapy program comprising the therapy parameter value.

Example 48: The storage medium of any of examples 38 through 47, wherein, to determine the therapy parameter value, the instructions cause the processing circuitry to apply a machine-learning model trained to identify the characteristic of the ECAP signal to produce the therapy parameter value, and wherein the therapy parameter value is configured to maintain a preferred ECAP signal characteristic.

Example 49: The storage medium of example 48, wherein, to apply the machine-learning model, the instructions cause the processing circuitry to: vary therapy parameter values of the first stimulation pulse until a desired patient condition is elicited; sense the ECAP signal at the time at which the desired patient condition is elicited; store a template indicative of the sensed ECAP signal; and vary therapy parameter values of the second stimulation pulse to maintain sensed ECAP signals consisted with the stored template.

Example 50: The storage medium of any of examples 38 through 49, wherein the instructions further cause the processing circuitry to receive sensor data from one or more sensors disposed at a location separate from the spinal cord, wherein, to determine the therapy parameter value, the processing circuitry is configured to determine the therapy parameter value based on the characteristic of the ECAP signal and based on the sensor data.

Example 51: The storage medium of example 50, wherein the one or more sensors comprise at least one of an accelerometer, an EEG, or an EMG.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
delivering first stimulation therapy configured to treat at least one symptom associated with prior damage to a spinal cord of a patient, the first stimulation therapy at least partially defined by a first value of a therapy parameter;
delivering, via a first electrode combination, a stimulation pulse to a portion of a spinal cord of the patient located caudally of a spinal cord injury location associated with the prior damage to the spinal cord of the patient;
sensing, via a second electrode combination, an evoked compound action potential (ECAP) signal elicited by the stimulation pulse;
identifying, by processing circuitry, a characteristic of the ECAP signal;
determining, by the processing circuitry and based on the characteristic of the ECAP signal, a second value of the therapy parameter that at least partially defines a second stimulation therapy configured to treat the at least one symptom associated with the prior damage to the spinal cord; and
delivering the second stimulation therapy to the patient according to the second value of the therapy parameter.

2. The method of claim 1, further comprising:
storing data indicative of a plurality of ECAP signals sensed over a time period, the plurality of ECAP signals comprising the ECAP signal; and
determining a trend from the data indicative of changes of the spinal cord of the patient over the time period.

3. The method of claim 1, wherein determining the second value of the therapy parameter for the second stimulation therapy comprises determining at least the second value of the therapy parameter that defines stimulation pulses that contribute to induction of a macro-function of the patient.

4. The method of claim 3, further comprising iteratively determining values of the therapy parameter for respective subsequent stimulation pulses based on characteristics of respective ECAP signals to induce a body function associated with the macro-function of the patient.

5. The method of claim 1, wherein the characteristic is a first characteristic and the ECAP signal is a first ECAP signal, and wherein the method further comprises:
determining a second characteristic of a second ECAP signal sensed via the electrode combination; and determining, based on the second characteristic of the second ECAP signal, to terminate delivery of at least the second stimulation therapy to induce a macro-function of the patient.

6. The method of claim 1, wherein the ECAP signal comprises a first ECAP signal, and wherein the method further comprises:

sensing, via a third electrode combination positioned cranially to the spinal cord injury location associated with the prior damage to the spinal cord, a second ECAP signal;

determining a characteristic of the third ECAP signal; and comparing the characteristic of the first ECAP signal sensed by the second electrode combination to the characteristic of the second ECAP signal sensed by the third electrode combination, wherein determining the second value of the therapy parameter comprises determining, based on the comparison, the second value of the therapy parameter.

7. The method of claim 1, wherein determining the second value of the therapy parameter comprises determining the second value of the therapy parameter to define one or more stimulation pulses comprising the second stimulation therapy to promote standing or locomotion of the patient.

8. The method of claim 1, wherein determining the second value of the therapy parameter comprises:

determining, based on the characteristic of the ECAP signal, a volitional intent of the patient; and selecting, based on the determined volitional intent, a therapy program comprising the second value of the therapy parameter.

9. The method of claim 1, wherein determining the second value of the therapy parameter comprises applying a machine-learning model trained to identify the characteristic of the ECAP signal to produce the second value of the therapy parameter, and wherein the second value of the therapy parameter is configured to maintain a preferred ECAP signal characteristic.

10. The method of claim 1, further comprising receiving sensor data from one or more sensors disposed at a location separate from the spinal cord, wherein determining the second value of the therapy parameter comprises determining the second value of the therapy parameter based on the characteristic of the ECAP signal and based on the sensor data.

11. The method of claim 1, further comprising:

determining an ECAP template representative of a detected ECAP signal associated with stimulation that treats the at least one symptom associated with the prior damage to the spinal cord; and storing the ECAP template in a memory, wherein determining the second value of the therapy parameter that at least partially defines the second stimulation therapy comprises:

determining that the characteristic of the ECAP signal does not correspond to the ECAP template stored in the memory; and responsive to determining that the characteristic does not correspond to the ECAP template, adjust the first value of the therapy parameter to the second value of the therapy parameter.

12. The method of claim 1, further comprising:

sensing a plurality of subsequent ECAP signals elicited by subsequent stimulation pulses;

identifying a respective characteristic for each ECAP signal of the subsequent ECAP signals; and iteratively adjusting, based on the respective characteristics of the ECAP signals, the therapy parameter that at least partially defines subsequent stimulation pulses to cause the respective characteristics of the subsequent ECAP signals to oscillate between a minimum target ECAP characteristic value and a maximum target ECAP characteristic value.

13. A system comprising:

stimulation generation circuitry configured to:

deliver first stimulation therapy configured to treat at least one symptom associated with prior damage to a spinal cord of a patient, the first stimulation therapy at least partially defined by a first value of a therapy parameter;

deliver, via a first electrode combination, a stimulation pulse to a portion of a spinal cord of the patient located caudally of a spinal cord injury location associated with the prior damage to the spinal cord of the patient; and processing circuitry configured to:

receive, via a second electrode combination, a sensed evoked compound action potential (ECAP) signal elicited by the stimulation pulse;

identify a characteristic of the ECAP signal;

determine, based on the characteristic of the ECAP signal, a second value of the therapy parameter that at least partially defines a second stimulation therapy configured to treat the at least one symptom associated with the prior damage to the spinal cord; and control the stimulation generation circuitry to deliver the second stimulation therapy to the patient according to the second value of the therapy parameter.

14. The system of claim 13, wherein the processing circuitry is further configured to:

store data indicative of a plurality of ECAP signals sensed over a time period, the plurality of ECAP signals comprising the ECAP signal; and determine a trend from the data indicative of changes of the spinal cord of the patient over the time period.

15. The system of claim 13, wherein, to determine the second value of the therapy parameter value for the second stimulation therapy, the processing circuitry is configured to determine at least the second value of the therapy parameter that defines stimulation pulses that contribute to induction of a macro-function of the patient.

16. The system of claim 15, wherein the processing circuitry is further configured to iteratively determine values of the therapy parameter for respective subsequent stimulation pulses based on characteristics of respective ECAP signals to induce a body function associated with the macro-function of the patient.

17. The system of claim 13, wherein, to determine the second value of the therapy parameter, the processing circuitry is configured to determine the second value of the therapy parameter to define one or more stimulation pulses comprising the second stimulation therapy to promote standing or locomotion of the patient.

18. The system of claim 13, wherein, to determine the second value of the therapy parameter, the processing circuitry is configured to:

determine, based on the characteristic of the ECAP signal, a volitional intent of the patient; and select, based on the determined volitional intent, a therapy program comprising the second value of the therapy parameter.

19. The system of claim 13, wherein, to determine the second value of the therapy parameter, the processing circuitry is configured to apply a machine-learning model trained to identify the characteristic of the ECAP signal to produce the second value of the therapy parameter, and wherein the second value of the therapy parameter is configured to maintain a preferred ECAP signal characteristic.

20. The system of claim 13, wherein the processing circuitry is further configured to receive sensor data from one or more sensors disposed at a location separate from the spinal cord, wherein, to determine the second value of the therapy parameter, the processing circuitry is configured to determine the second value of the therapy parameter based on the characteristic of the ECAP signal and based on the sensor data.

21. The system of claim 13, further comprising an implantable medical device comprising the processing circuitry and the stimulation generation circuitry.

\* \* \* \* \*